United States Patent
Golden et al.

(12) 
(10) Patent No.: US 6,695,859 B1
(45) Date of Patent: Feb. 24, 2004

(54) APPARATUS AND METHODS FOR ANASTOMOSIS

(75) Inventors: Steve Golden, Menlo Park, CA (US); John Nguyen, San Jose, CA (US); Charles T. Maroney, Portola Valley, CA (US); Sid Gandionco, Fremont, CA (US); Laurent Schaller, Los Altos, CA (US); Liem Ho, Mountain View, CA (US)

(73) Assignee: Coalescent Surgical, Inc., Sunnyvale, CA (US)

( * ) Notice: Subject to any disclaimer, the term of this patent is extended or adjusted under 35 U.S.C. 154(b) by 0 days.

(21) Appl. No.: 09/540,636

(22) Filed: Mar. 31, 2000

Related U.S. Application Data

(60) Provisional application No. 60/127,862, filed on Apr. 5, 1999.

(51) Int. Cl.[7] ............................................. A61B 17/32
(52) U.S. Cl. ........................ 606/184; 606/153; 606/159
(58) Field of Search ............................... 606/179, 184, 606/185, 213, 153, 232; 604/164.03, 164.04, 164.06, 164.01; 600/566, 567

(56) References Cited

U.S. PATENT DOCUMENTS

| | | |
|---|---|---|
| 1,167,014 A | 1/1916 | O'Brien |
| 1,867,624 A | 7/1932 | Hoffman |
| 2,505,358 A | 4/1950 | Gusberg et al. |
| 3,776,237 A | 12/1973 | Hill et al. |
| 3,837,345 A | 9/1974 | Matar |
| 4,018,228 A | 4/1977 | Goosen |
| 4,243,048 A | 1/1981 | Griffin |
| 4,523,592 A | 6/1985 | Daniel |
| 5,035,702 A | 7/1991 | Taheri |
| 5,119,983 A | 6/1992 | Green et al. |
| 5,129,913 A | 7/1992 | Ruppert |
| 5,178,634 A | 1/1993 | Ramos Martinez |
| 5,192,294 A | 3/1993 | Blake |
| 5,221,259 A * | 6/1993 | Weldon et al. ............... 606/213 |
| 5,304,117 A | 4/1994 | Wilk |
| 5,314,468 A | 5/1994 | Ramos Martinez |
| 5,346,459 A | 9/1994 | Allen |
| 5,353,804 A | 10/1994 | Kornberg et al. |
| 5,355,897 A | 10/1994 | Pietrafitta et al. |
| 5,403,338 A | 4/1995 | Milo |

(List continued on next page.)

FOREIGN PATENT DOCUMENTS

| | | |
|---|---|---|
| DE | 197 32 234 A1 | 1/1999 |
| WO | WO 92/12676 A2 | 8/1992 |
| WO | WO 97/12555 | 4/1997 |
| WO | WO 97/16122 | 5/1997 |
| WO | WO 97/27898 | 8/1997 |
| WO | WO 97/31575 | 9/1997 |
| WO | WO 97/40754 | 11/1997 |
| WO | WO 98/19636 A3 | 5/1998 |
| WO | WO 98/42262 A1 | 10/1998 |
| WO | WO 98/48707 A1 | 11/1998 |

(List continued on next page.)

OTHER PUBLICATIONS

US 5,826,777, 10/1998, Green et al. (withdrawn).
International Preliminary Examination Report PCT/US00/09092, Jun. 19, 2003.

(List continued on next page.)

*Primary Examiner*—Julian W. Woo
(74) *Attorney, Agent, or Firm*—Harry J. Macey

(57) ABSTRACT

Apparatus and methods for performing an anastomosis. More particularly, the apparatus may be used to perform a single or multiple anastomosis with the ability of maintaining fluid flow (e.g., blood) through the anastomosis vessel according to one aspect of the invention.

30 Claims, 26 Drawing Sheets

U.S. PATENT DOCUMENTS

| | | |
|---|---|---|
| 5,445,644 A | 8/1995 | Pietrafitta et al. |
| 5,452,733 A | 9/1995 | Sterman et al. |
| 5,488,958 A | 2/1996 | Topel et al. |
| 5,538,509 A | 7/1996 | Dunlap et al. |
| 5,556,411 A | 9/1996 | Taoda et al. |
| 5,569,205 A | 10/1996 | Hart et al. |
| 5,643,305 A | 7/1997 | Al-Tameem |
| 5,653,718 A | 8/1997 | Yoon |
| 5,660,186 A | 8/1997 | Bachir |
| 5,669,918 A | 9/1997 | Balazs et al. |
| 5,676,670 A | 10/1997 | Kim |
| 5,690,662 A | 11/1997 | Chiu et al. |
| 5,695,504 A | 12/1997 | Gifford, III et al. |
| 5,697,913 A | 12/1997 | Sierocuk et al. |
| 5,702,412 A | 12/1997 | Popov et al. |
| 5,707,380 A | 1/1998 | Hinchliffe et al. |
| 5,709,693 A | 1/1998 | Taylor |
| 5,732,872 A | 3/1998 | Bolduc et al. |
| 5,755,778 A | 5/1998 | Kleshinski |
| 5,769,870 A | 6/1998 | Salahich et al. |
| 5,797,920 A | 8/1998 | Kim |
| 5,797,933 A | 8/1998 | Snow et al. |
| 5,797,934 A | 8/1998 | Rygaard |
| 5,799,661 A | 9/1998 | Boyd et al. |
| 5,799,857 A | 9/1998 | Robertson et al. |
| 5,817,113 A | 10/1998 | Gifford, III et al. |
| 5,824,002 A | 10/1998 | Gentelia et al. |
| 5,827,265 A | 10/1998 | Glinsky et al. |
| 5,827,316 A | 10/1998 | Young et al. |
| 5,830,222 A | 11/1998 | Makower |
| 5,833,698 A | 11/1998 | Hinchliffe et al. |
| 5,851,216 A | 12/1998 | Allen |
| 5,868,702 A | 2/1999 | Stevens et al. |
| 5,868,763 A | 2/1999 | Spence et al. |
| 5,881,943 A | 3/1999 | Heck et al. |
| 5,882,340 A | 3/1999 | Yoon |
| 5,893,369 A | 4/1999 | LeMole |
| 5,893,865 A | 4/1999 | Swindle et al. |
| 5,904,697 A | 5/1999 | Gifford, III et al. |
| 5,941,908 A | 8/1999 | Goldsteen et al. |
| 5,944,730 A | 8/1999 | Nobles et al. |
| 5,954,735 A | 9/1999 | Rygaard |
| 5,957,363 A | 9/1999 | Heck |
| 5,976,164 A | 11/1999 | Bencini et al. |
| 5,989,276 A | 11/1999 | Houser et al. |
| 5,989,278 A | 11/1999 | Mueller |
| 5,993,468 A | 11/1999 | Rygaard |
| 6,007,544 A | 12/1999 | Kim |
| 6,022,367 A | 2/2000 | Sherts |
| 6,033,419 A | 3/2000 | Hamblin, Jr. et al. |
| 6,036,703 A | 3/2000 | Evans et al. |
| 6,036,710 A | 3/2000 | McGarry et al. |
| 6,080,114 A | 6/2000 | Russin |
| 6,083,237 A | 7/2000 | Huitema et al. |
| 6,106,538 A | 8/2000 | Shiber |
| 6,171,321 B1 | 1/2001 | Gifford, III et al. |
| 6,280,460 B1 | 8/2001 | Bolduc et al. |
| 6,346,074 B1 | 2/2002 | Roth |
| 6,387,105 B1 | 5/2002 | Gifford, III et al. |
| 6,409,739 B1 | 6/2002 | Nobles et al. |
| 6,416,527 B1 | 7/2002 | Berg et al. |
| 6,428,555 B1 | 8/2002 | Koster, Jr. |
| 2001/0021856 A1 | 9/2001 | Bolduc et al. |
| 2002/0042623 A1 | 4/2002 | Blatter et al. |
| 2002/0082614 A1 | 6/2002 | Logan et al. |

FOREIGN PATENT DOCUMENTS

| | | |
|---|---|---|
| WO | WO 98/52475 A1 | 11/1998 |
| WO | WO98/52475 | 11/1998 |
| WO | WO 99/07294 A1 | 2/1999 |
| WO | WO 99/12484 A1 | 3/1999 |
| WO | WO 99/15088 | 4/1999 |
| WO | WO 99/37218 | 7/1999 |
| WO | WO 99/62408 | 12/1999 |
| WO | WO 99/62415 | 12/1999 |
| WO | WO 99/63910 | 12/1999 |
| WO | WO 99/65409 | 12/1999 |
| WO | WO 00/15144 | 3/2000 |

OTHER PUBLICATIONS

Written Opinion PCT/US00/09092 of Apr. 1, 2003.
International Search Report PCT/US00/09092.

* cited by examiner

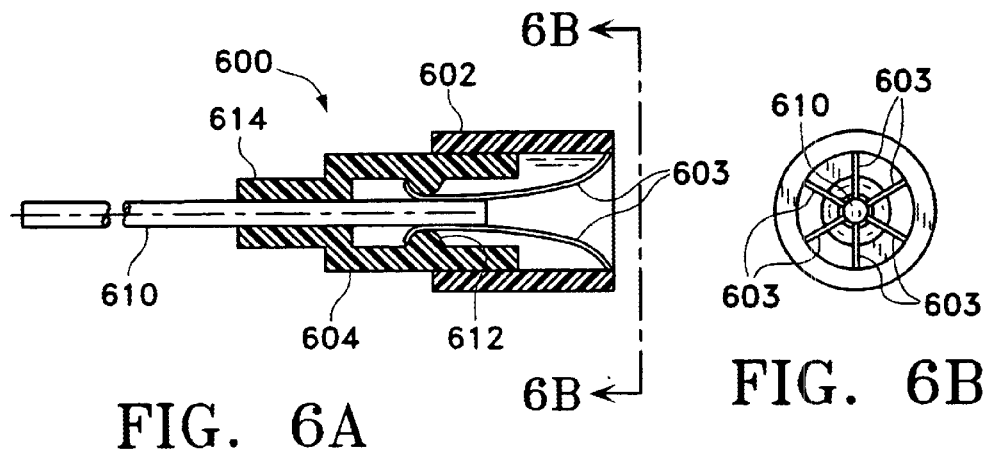
FIG. 6A
FIG. 6B
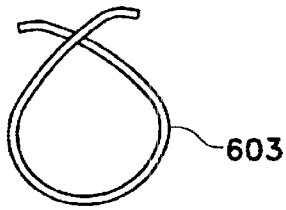
FIG. 6C
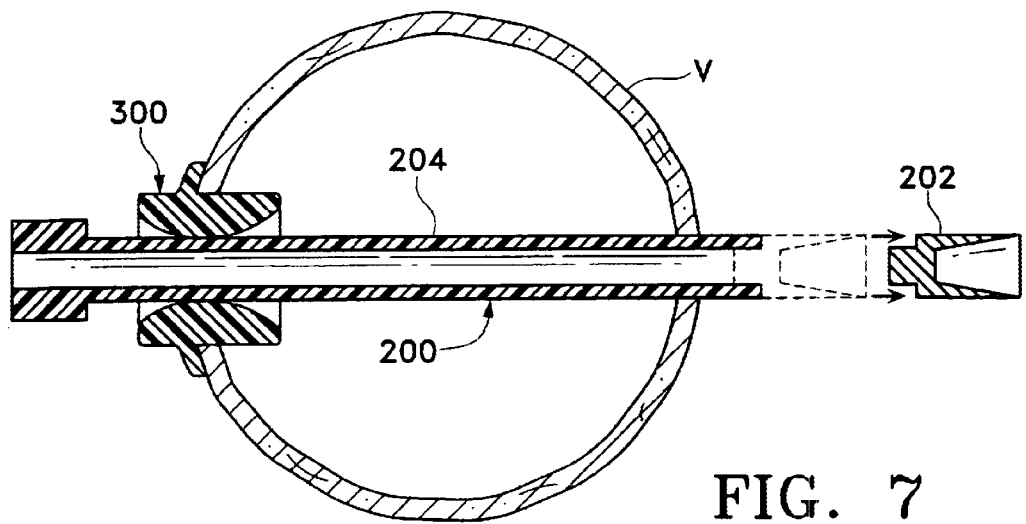
FIG. 7

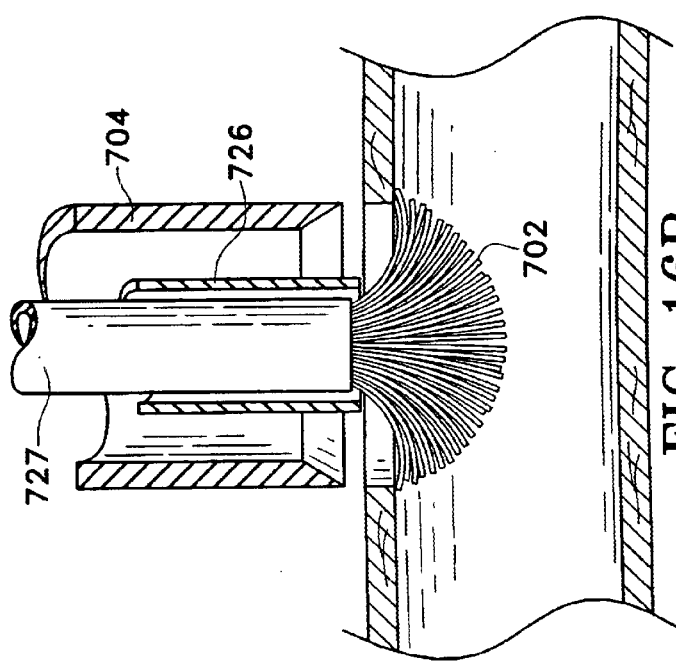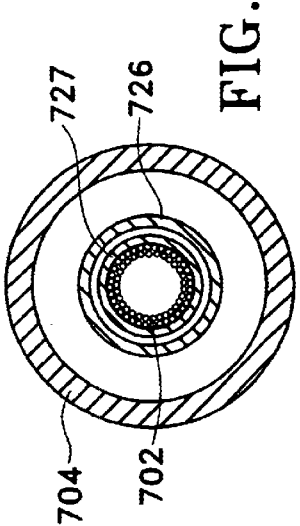
FIG. 16B
FIG. 16D
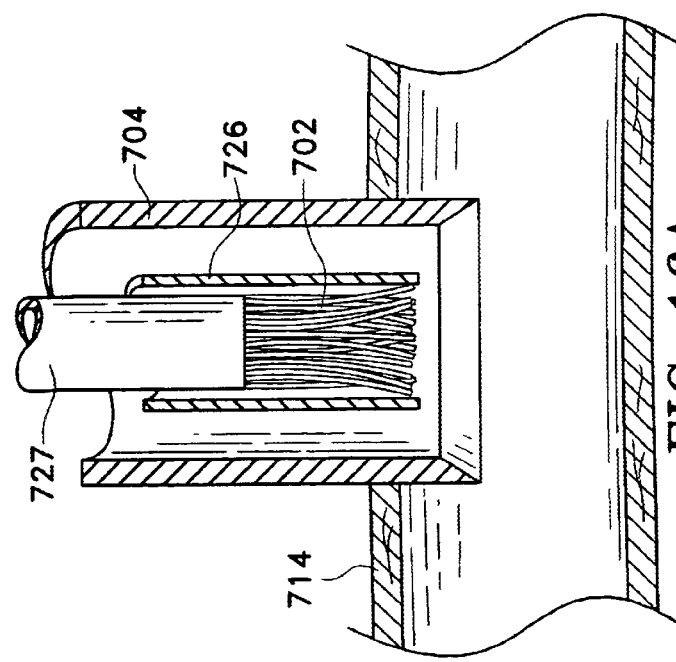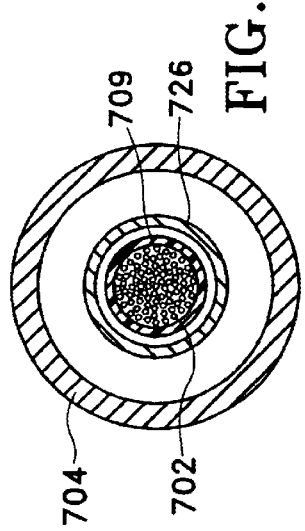
FIG. 16A
FIG. 16C

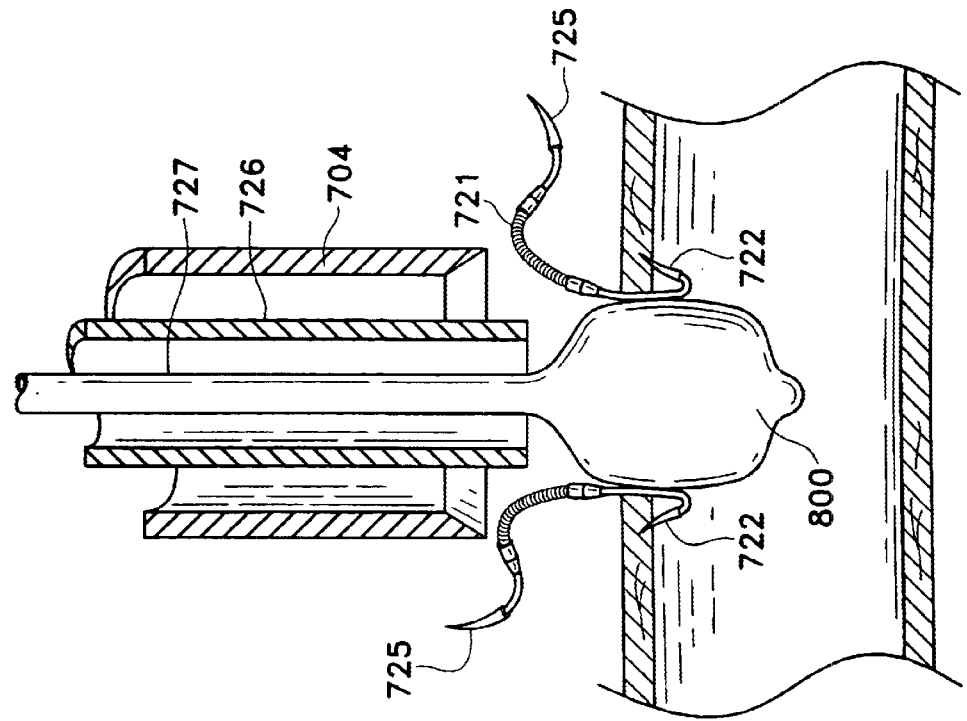
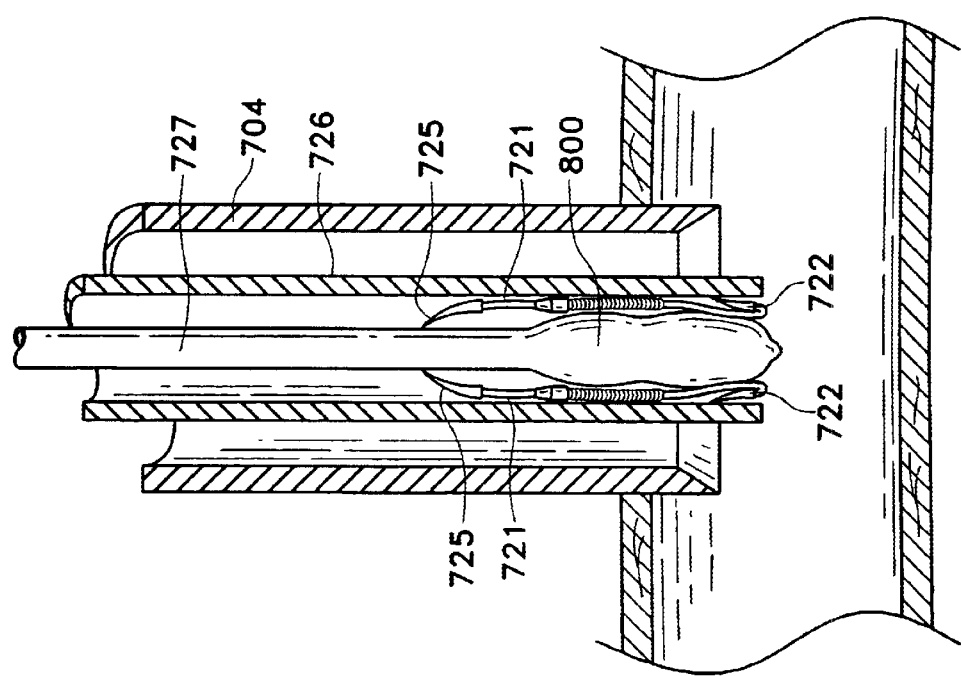

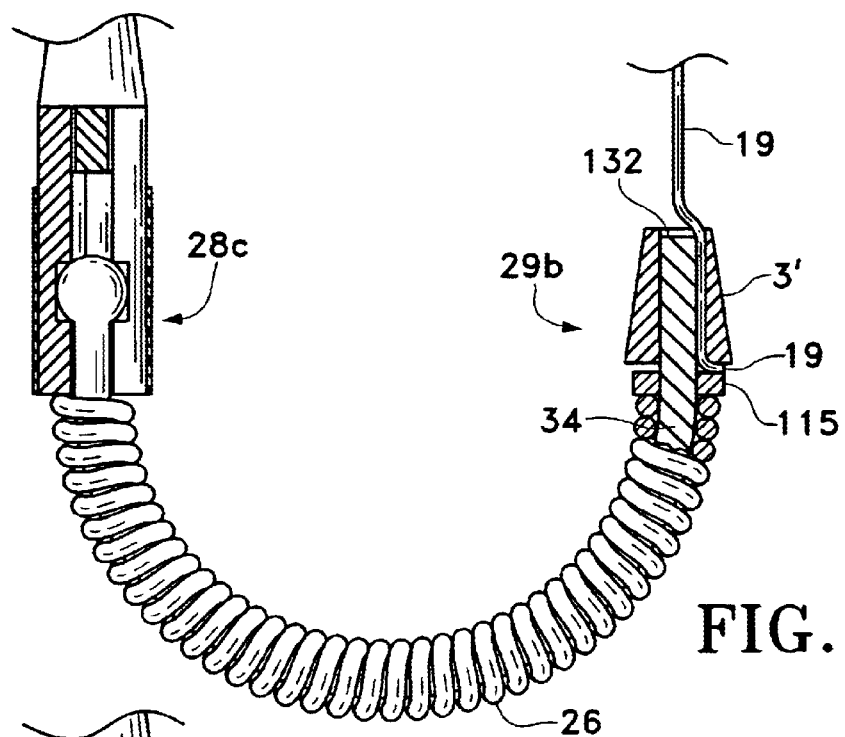
FIG. 17I
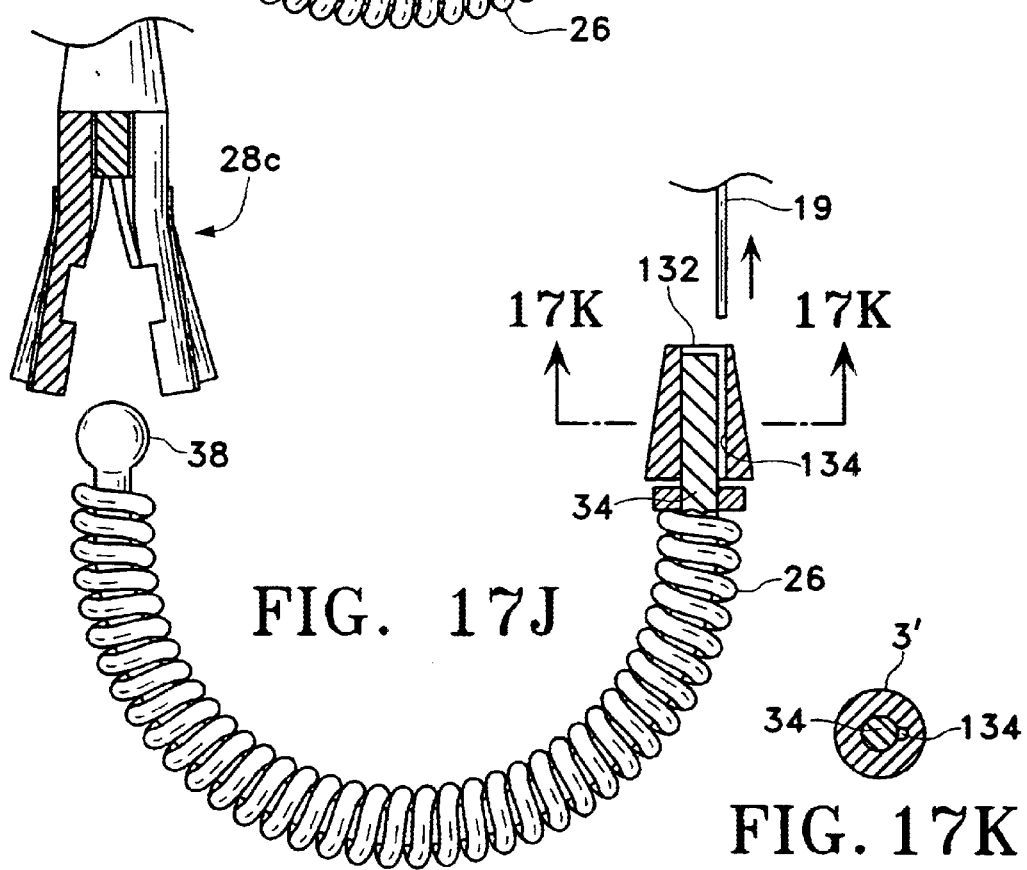
FIG. 17J
FIG. 17K

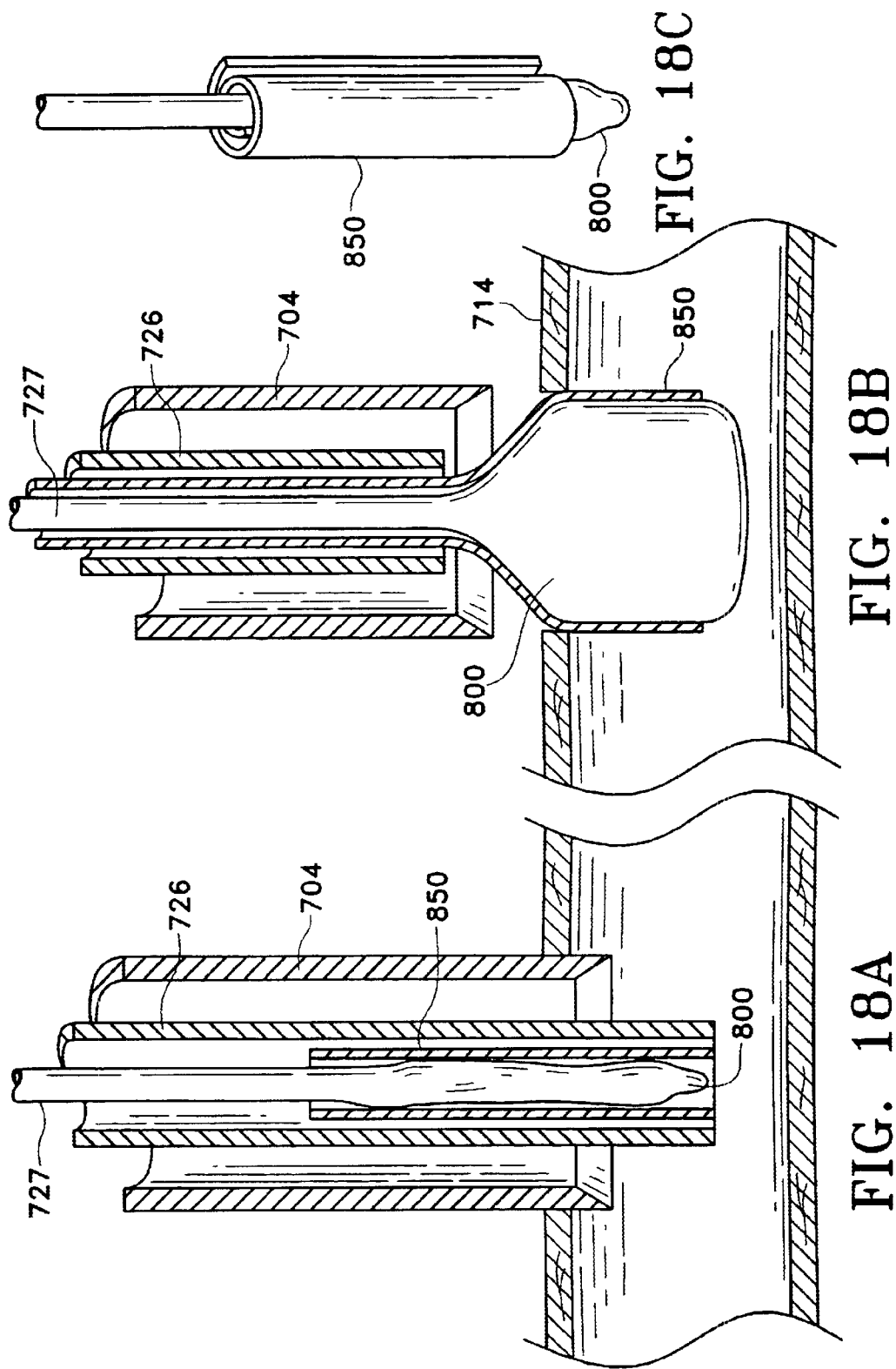

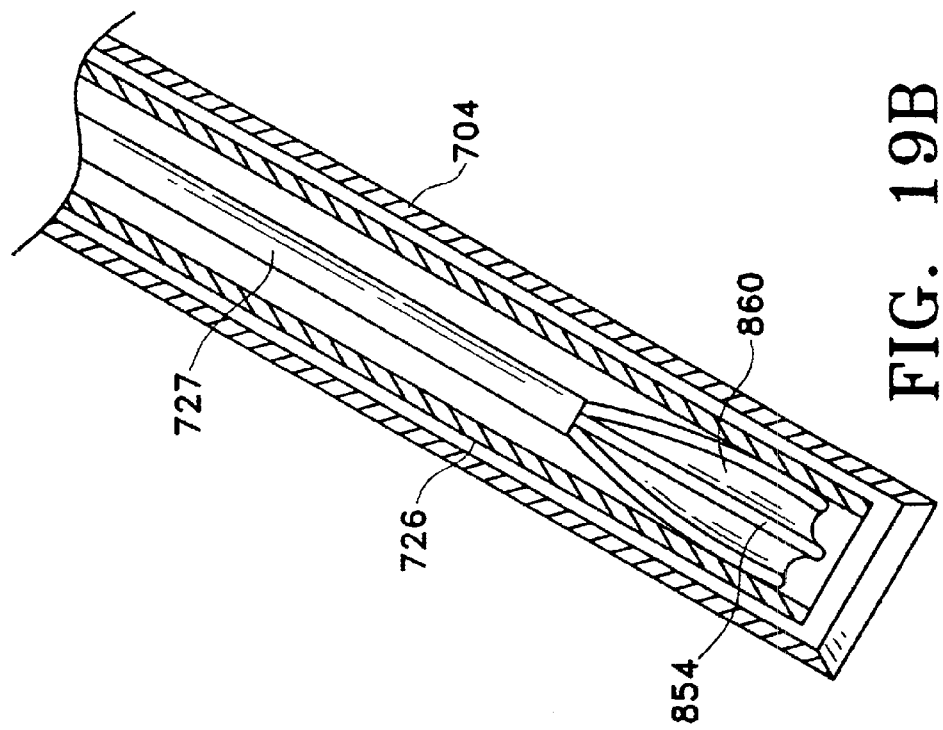
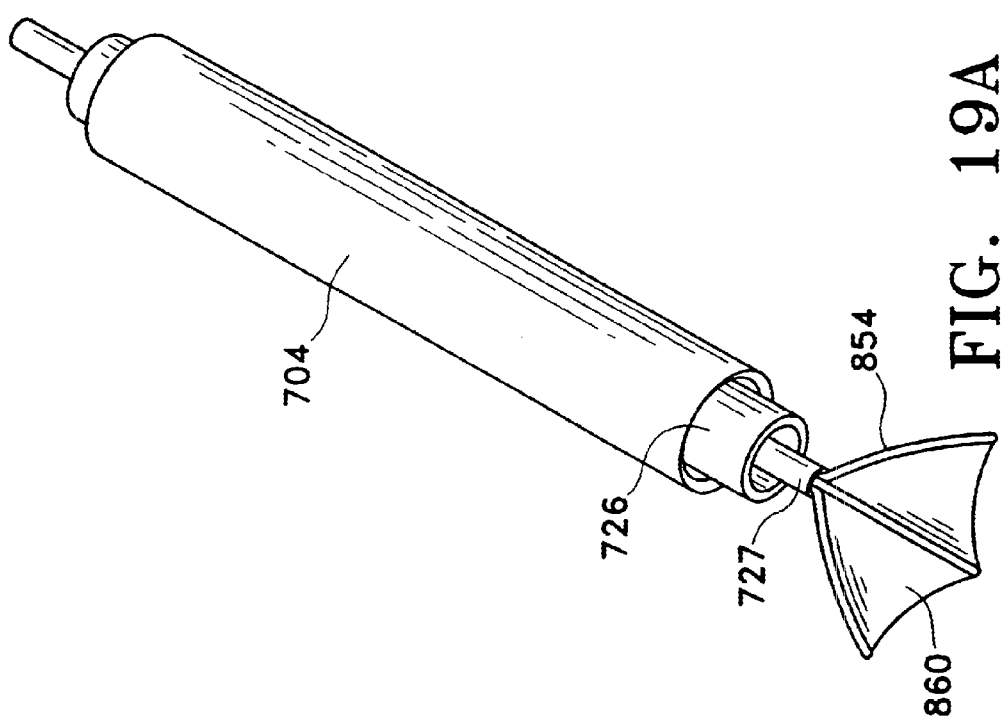
FIG. 19B
FIG. 19A

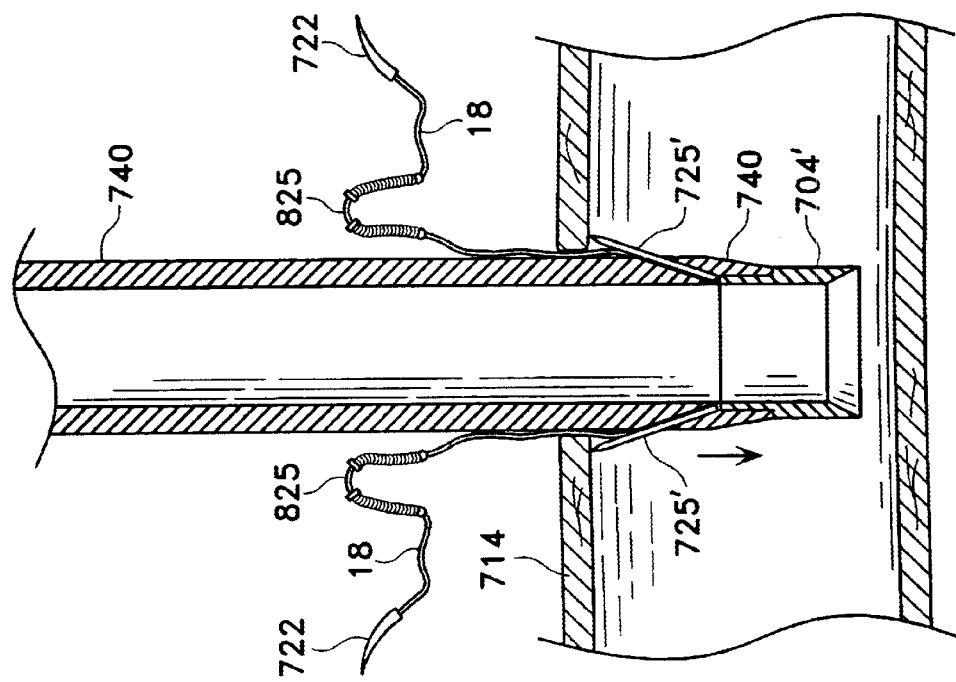
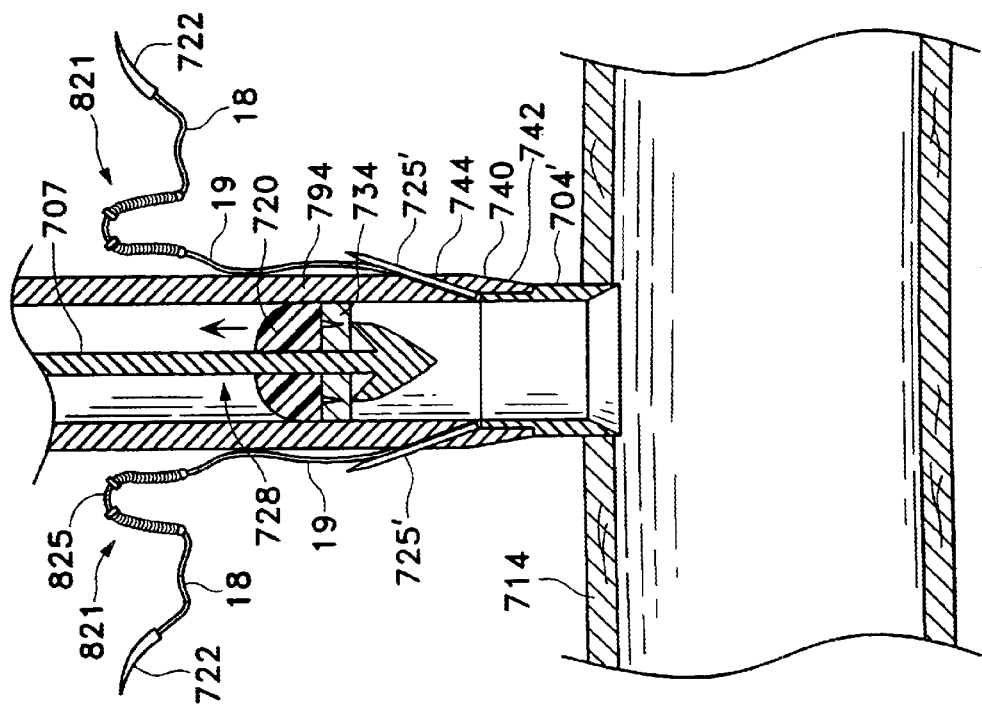

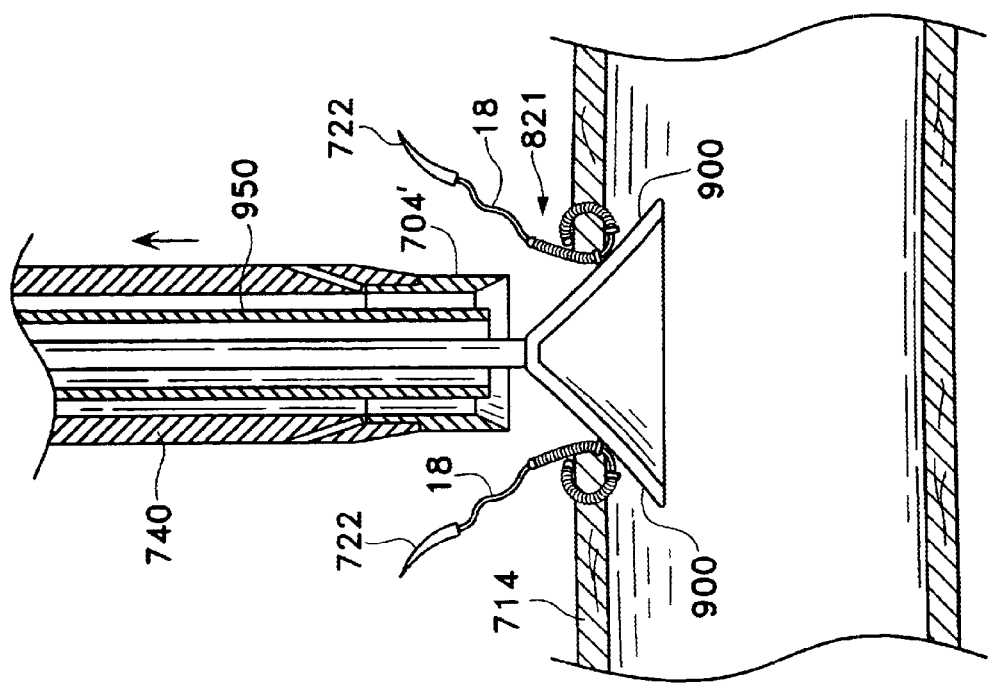
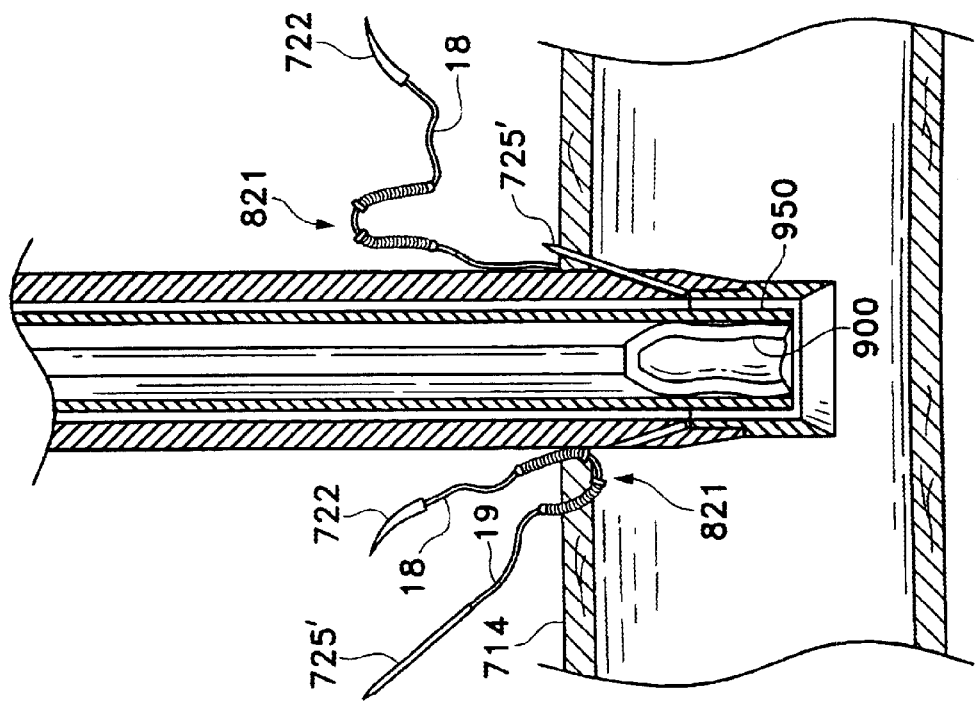

APPARATUS AND METHODS FOR ANASTOMOSIS

CROSS-REFERENCE TO RELATED APPLICATIONS

This application hereby claims priority to copending provisional application Ser. No. 60/127,862, which was filed on Apr. 5, 1999, and which is hereby incorporated herein, by reference thereto, in its entirety.

FIELD OF THE INVENTION

The present invention relates to apparatus and methods for performing an anastomosis. The apparatus may be used to perform a single or multiple anastomosis with the ability of maintaining fluid flow (e.g., blood) through the anastomosis vessel.

BACKGROUND OF THE INVENTION

The occlusion of the arteries can lead to insufficient blood flow resulting in discomfort and risks of angina and ischemia. Significant blockage of blood flow in the coronary artery can result in damage to the myocardial tissue or death of the patient. In most cases, occlusion of the artery results from progressive long term deposits of plaque along the artery wall. While such deposits may be concentrated and occlude the artery at a particular site, the deposits are most certainly present throughout the arteries and the vascular system.

Coronary artery bypass graft (CABG) surgery is a surgical procedure performed in severe cases of coronary blockages. CABG procedures involve anastomosing an artery to a vascular graft which restores the flow of blood by establishing another pathway around the occluded vasculature. One problem encountered in the procedure is the need of performing the procedure while simultaneously maintaining sufficient function of the patient's circulatory system.

A CABG procedure may involve arresting the heart so that blood flow is diverted from the vessel to be anastomosed. The patient's blood circulation is maintained by a cardiopulmonary bypass (CPB). This bypass is accomplished by diverting the blood flow at selected arterial locations. The blood is diverted to the bypass system for release of carbon dioxide and subsequent oxygenation. Then, the blood is returned to the patient via a pump. Examples of these procedures are found in U.S. Pat. No. 5,799,661 to Boyd et al. which discloses a device and method for performing CABG surgery for multi-vessel coronary artery disease through port-access or closed-chest thoroscopic methods; and U.S. Pat. No. 5,452,733 to Sterman et al. which discusses performing grafts with an efficacy equal to or greater than conventional open surgical bypass techniques.

Another CABG procedure involves operating on a beating heart and eliminates the need for a CPB. However, the procedure still requires diverting blood flow for a proximal anastomosis, such as one which attaches graft material (e.g., a graft vessel) to the ascending aorta.

First, the blood flow may be diverted by aortic clamping. Among the drawbacks associated with aortic clamping are an increased chance of trauma to the arteries caused by ligatures at the clamped site and the possible dislodging of plaque within the clamped vessel wall. As mentioned above, the arterial bypass may be required due to the deposits of plaque which have occluded the vessel. However, the plaque is typically present throughout the artery and is not limited to the occluded location. Clamping the artery creates a risk of plaque being released into the blood stream. This release of plaque has the potential of causing a stroke, occlusion of a smaller peripheral vessel, or other vascular trauma. In a beating heart procedure, full clamping (i.e., cross clamping) of the aorta for graft attachment at the proximal anastomosis is not feasible. Therefore a side biting clamp is used to clamp off only a portion of the cross-section of the aorta, where the proximal anastomosis is performed. This type of clamping procedure poses the same risks described above with regard to cross clamping, e.g., the risk of release of plaque and resultant cause of a stroke, occlusion of a smaller peripheral vessel, or other vascular trauma.

Second, the blood flow may be diverted by the use of a balloon catheter within the aorta, such as described in U.S. Pat. No. 5,868,702, for example. Drawbacks of using a balloon catheter in creating a seal to divert blood flow include the possibility of disturbing plaque deposits and creating particles in the blood stream, the chance that the balloon catheter may move within the aorta disrupting the seal and resulting in blood loss, and trauma to aortic tissue caused by the pressure needed to create the seal.

PCT Patent WO 98/52475 to Nobles et al. attempts to address problems associated with diverting the blood flow. Nobles et al. provides a method and device for creating an area of hemostasis within a blood vessel without interrupting the flow of blood through the vessel which eliminates the need to clamp the vessel. However, the Nobles et al. device requires the withdrawal of the hemostasis device prior to obtaining a tight seal between the graft and vessel. Therefore, since the area of hemostasis is lost upon the retrieval of the hemostasis device, the artery is open and blood is lost until the sutures are tightened.

Yet another problem related to CABG procedure lies in the procedure of suturing the vessels to create a tight seal. To ensure the integrity and patency of the anastomosis, the graft and vessel to be joined must be precisely aligned with respect to each other. If one of the tissues is affixed too close to its edge, the suture can tear through the tissue and impair both the tissue and the anastomosis. Another problem is that, even after proper alignment of the tissue, it is difficult and time consuming to pass the needle through the tissues, form the knot with the suture material, and ensure that the suture material does not become entangled. These difficulties are exacerbated by the small size of the artery and graft. Another factor contributing to the difficulty of the CABG procedure is the limited time available to complete the procedure. The surgeon must complete the graft in as little time possible due to the absence of blood flowing through the artery. If blood flow is not promptly restored, sometimes in as little as 30 minutes, the tissues the artery supplies may experience significant damage or necrosis. As mentioned above, surgeons are under pressure to reduce the cross-clamp time, yet, an incomplete suture may result in a leak in the tissue approximation between the vessel and graft. Moreover, the tissue approximation must be smooth and open. Hence, the suture cannot be hastily performed.

Additionally, the difficulty of suturing a graft to an artery using minimally invasive surgical techniques, where the surgeon uses ports to access the internal organs to perform the procedure, has effectively prevented the safe use of complicated suturing technology in cardiovascular surgical procedures. Accordingly, many procedures are performed invasively and require a sternotomy, an opening of the sternum. As a result, the recovery times for patients is significantly increased. U.S. Pat. No. 5,868,763 to Spence et al. attempts to circumvent the suturing process by attaching the vessels to a cuff device. Spence et al. utilizes a passageway for continued blood flow so there is no clamping of the artery.

Houser et al., in U.S. Pat. No. 5,989,276, discloses various devices and techniques for performing bypass, one of which includes a device which can be intralumenally originated. Various other clamping arrangements are provided for securing a graft to a vessel without the use of sutures or other fasteners.

All of the problems discussed above are multiplied in those cases where a multiple anastomosis is required. In those cases where multiple bypass procedures are performed, the patient will naturally be subject to increased risks as multiple grafts must be sutured to perform the bypass.

There remains a need for improved anastomosis systems.

SUMMARY OF THE INVENTION

The present invention involves apparatus and methods for connecting tissue. This invention may, for example, be used to secure one vessel to another, such as in a vascular anastomosis while maintaining blood flow within the vessel.

According to one aspect of the invention, an anastomosis apparatus is provided comprising a tubular member having an end with an edge adapted to form an opening in a vessel wall and an anchor member, which comprises a flexible shaft and a piercing member, slidably coupled to the tubular member. Preferably, a generally circular centering disk with a plurality of spikes is also provided to slide down along the flexible shaft of the anchor member.

During the surgery, a physician pushes the shaft of the anchor member to insert the piercing member through the vessel wall. The piercing member is then pulled back against the vessel wall. Once the piercing member is in place against the inner wall of the vessel, the centering disk is put in place and pushed against the outer wall of the vessel, thereby clamping the vessel wall between the centering disk and the piercing member. The tubular member is then moved over the shaft, centered by the disk and rotated to cut an opening through the vessel wall. Thereafter, the piercing member is used to coordinate with the centering disk to retain and retrieve the tissue cut by the tubular member. Next, an occlusion member is advanced within the tubular member through the opening in the vessel wall in order to substantially occlude such opening and form an area of hemostasis. The tubular member can then be retrieved, leaving the occlusion member in place, after which a graft is slid down along the occlusion member shaft for creating an anastomosis with the vessel.

According to one embodiment, the occlusion member comprises a cannula. According to another embodiment, the occlusion member comprises a radially expandable member, which can be an expandable brush-like member, an umbrella, a flexible cup or an inflatable balloon.

According to another aspect of the invention a cannula having an end portion adapted to pierce through a vessel is provided. The cannula may be passed through a vessel wall and a graft secured to the vessel adjacent to the cannula to facilitate an anastomosis without clamping the vessel, thereby avoiding the risk of dislodgment of plaque from the inner wall of the vessel which is incurred with clamping.

According to another aspect of the invention, a trocar adapted to receive the cannula and allow it to pivot is provided. The cannula, thus, may be repositioned to pierce the vessel wall at different locations and perform multiple anastomoses without relocation of the trocar in the vessel wall.

According to another aspect of the invention, a surgical fastener or clip cartridge is provided. One or more surgical fasteners may be loaded in the cartridge with ends of each fastener selectively releasable from the cartridge to anchor in either the graft or vessel to which the graft is to be attached. According to one cartridge embodiment, first and second tubular members are slidably coupled to one another and at least one surgical fastener placed therein with one end of the fastener engaging the first tubular member and another end of the fastener engaging the second tubular member.

According to yet another aspect of the invention, a dual-stage release fastener is provided which includes a clip movable between an open and a closed configuration and having a memory biased to the closed configuration. A first mechanical restraint is coupled to a first portion of the clip and is adapted to bias the first portion toward the open configuration. A second mechanical restraint is coupled to a second portion of the clip and is adapted to bias the second portion toward the open configuration.

The first and second mechanical restraints may be independently manipulatable to allow independent closure of the first and second portions of the clip.

According to still another aspect of the invention, an anastomosis apparatus is provided comprising a tubular member having an end with an edge adapted to form an opening in a vessel wall and an anchor member, which comprises a flexible shaft and a piercing member, slidably coupled to the tubular member. Preferably, a generally circular centering disk with a plurality of spikes is also provided to slide down along the flexible shaft of the anchor member. An adapter is mounted on the tubular member that forms the opening. The adapter includes wells in which needles are held in a predetermined orientation adapted for piercing through the vessel wall from the inside out, upon passing the adapter into the vessel and then pulling it back to perform the piercing action. Two-stage release fasteners may be used in conjunction with the adapter so as to affix the fasteners to the vessel after piercing it with the needles and then fixing the fasteners to a graft in a later operation.

The above is a brief description of some advantages of the present invention and deficiencies in the prior art. Other features, advantages, and embodiments of the invention will be apparent to those skilled in the art from the following description, accompanying drawings, and claims.

BRIEF DESCRIPTION OF THE DRAWINGS

FIG. 6A is a partial sectional view of a configuration of a surgical fastener cartridge according to the present invention.

FIG. 6B is a front view of the cartridge of FIG. 6A.

FIG. 6C is a plan view of one of the surgical fasteners of FIGS. 6A and 6B in a released state.

FIGS. 7–11 show a method of preparing an anastomosis in accordance with the principles of the present invention.

FIG. 7 shows a sectional view of the trocar and cannula of FIG. 2 positioned in an artery with the piercing element removed.

FIG. 8 shows a sectional view of the placement of a graft over the cartridge of FIG. 6A.

FIG. 9 shows a sectional view of the partial release of the assembly of FIG. 8 with one end of the fasteners released and anchored to the graft.

FIG. 10 illustrates the complete removal of the tubular member which restrains the released fastener end.

FIG. 11 shows aligning and introducing the cartridge into the cannula.

FIG. 16A is a sectional view of another proximal anastomosis device, with a radially expandable member comprising a plurality of bristles.

FIG. 16B is a sectional view of the device of FIG. 16A, with the plurality of bristles radially expanded to occlude the opening in the vessel wall after the outer cylinder is withdrawn.

FIG. 16C is an end view of the device of FIG. 16A with a retaining ring attached to the inner cylinder to bind a bundle of bristles.

FIG. 16D is an end view of the device of FIG. 16A with the bristles attached to the inner wall of the hollow inner cylinder.

FIG. 17A is a sectional view of another proximal anastomosis device, with a radially expandable member comprising an inflatable membrane and a plurality of fasteners attached to the membrane.

FIG. 17B is a sectional view of the device of FIG. 17A with the membrane inflated to occlude the opening in the vessel wall.

FIGS. 17E–17K are detailed drawings of a fastener and portions thereof, which may be used in connecting grafts to vessels, according to the present invention.

FIG. 18A is a sectional view of another proximal anastomosis device, with a flexible sheath capable of expanding with the membrane.

FIG. 18B is a sectional view of the device of FIG. 18A with sheath expanded with the inflated membrane.

FIG. 18C is a view of a roll-up sheath with an expandable membrane therein.

FIG. 19A is a perspective view of another proximal anastomosis device comprising a skeleton which supports an umbrella-like occlusion member.

FIG. 19B is a sectional view of the device of FIG. 19A with the umbrella-like occlusion member in a folded state within the outer cylinder.

FIG. 20A is a sectional view of another example of a proximal anastomosis device with a punch, an anchor member and a centering disk.

FIG. 20B is a sectional view of the device of FIG. 20A after the tissue cut has been retrieved and the punch or cutting member has been further inserted within the vessel.

FIG. 20C is a sectional view of the device of FIG. 20A with an occlusion member inserted into the vessel and the cutting member having been pulled back to push the protruding needles through the vessel wall.

FIG. 20D is a sectional view of the device of FIG. 20A with the punch or cutting member retrieved and the occluding member in place, in preparation for placement of a graft. 2

DETAILED DESCRIPTION OF THE INVENTION

The present invention generally involves methods and apparatus for performing an anastomosis and may be used, for example, in bypass procedures. As used herein, the term graft includes any of the following: hemografts, autologous grafts, xenografts, allografts, alloplastic materials, and combinations of the foregoing.

Figure 1:
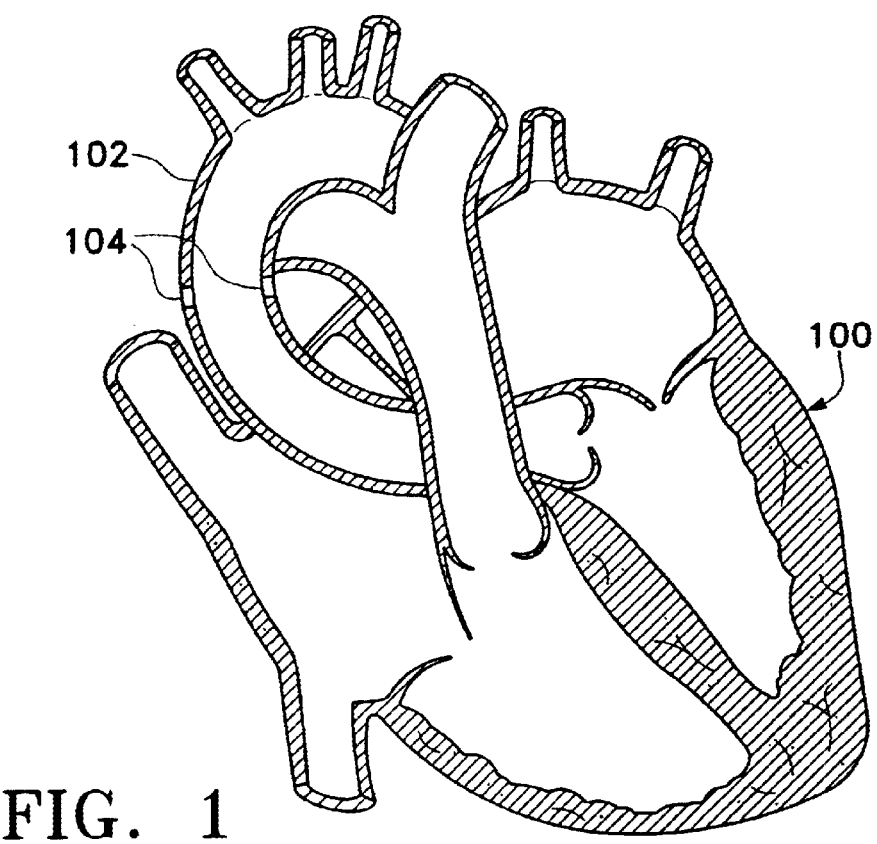
FIG. 1 is a sectional view of a heart illustrating an example of an anastomosis and trocar placement site.

Referring to FIG. 1, a heart (100) is shown in section with the aorta designated with reference numeral (102). One possible anastomosis site is on aorta (102). Two openings, generally designated with reference numeral (104), indicate where a cannula (described below) may be positioned to facilitate the anastomosis. It should be understood, however, that although an aortic anastomosis site is shown, the invention can be used in other areas of the human anatomy where one desires to connect a graft to tissue, or tubular structure.

According to one aspect of the invention, a cannula having a distal portion adapted to pierce at least one wall portion of a vessel and a proximal portion is provided. The cannula may be used, for example, to create an area of hemostasis within the vessel and facilitate an anastomosis while allowing blood to flow through the vessel. In a preferred method, the cannula is passed through a vessel wall from the interior to the exterior of the vessel to create a hemostasis area within the cannula and within the vessel hole created thereby, as will be described in more detail below.

Figure 2:
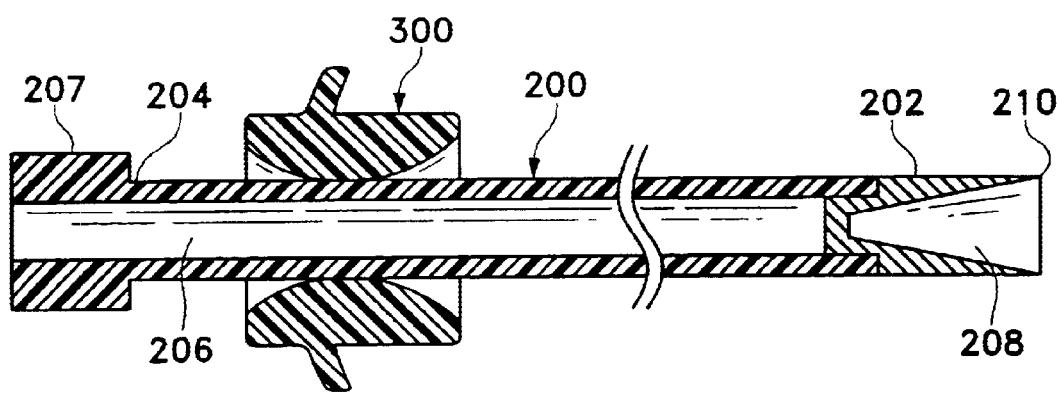
FIG. 2 is a sectional view of a cannula constructed according to the principles of the present invention and disposed within a trocar having a configuration according to another aspect of the invention.

Referring to FIG. 2, a cannula constructed according to the principles of the present invention is shown and generally designated with reference numeral (200). Cannula (200) generally includes a distal portion (202) adapted to pierce tissue and a proximal portion (204). Cannula (200) includes lumen (206) which extends the entire length of proximal portion (204). Lumen (206) allows access inside or through a vessel, while cannula (200) forms an area of hemostasis upon insertion of cannula (200) through a portion of a vessel wall. The distal portion of the cannula is configured to pierce tissue, and may comprise a member having a generally cylindrical outer surface and a tapered inner surface which forms a generally frustoconically shaped cavity (208). The distal end (210) of distal portion (202) tapers to an annular point. A proximal end (204) of the cannula is shown to have an expanded diameter. The length of the cannula (200) may vary depending on, for example, the size of the anastomosed vessels. It is further noted that although the distal and proximal portions (202, 204) are shown as separate elements, they may be integrally formed as a single unit to form the cannula (200). The proximal and distal portions may be constructed from a variety of materials. For example, the proximal portion may be plastic. It also may be constructed to be flexible so that it may be delivered endovascularly. In addition, the distal portion may be metal such as stainless steel.

Figure 3:
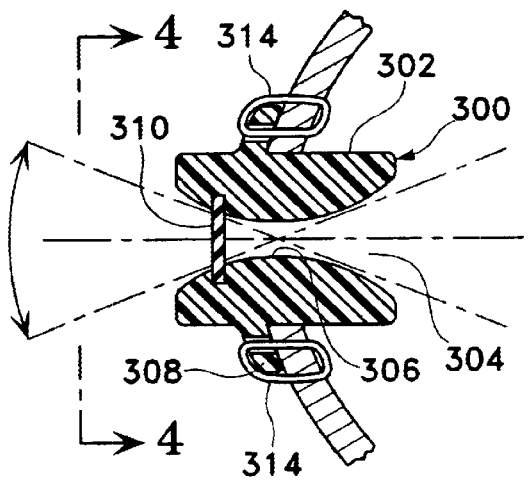
FIG. 3 is a partial sectional view of the trocar of FIG. 2.
Figure 4:
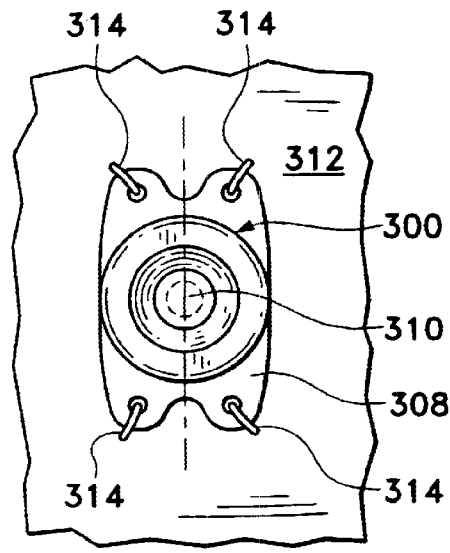
FIG. 4 is a side view of the trocar positioned on a vessel wall.

The cannula may be introduced endovascularly or passed through a vessel wall to position it within a vessel. In the latter case, a trocar may be used. According to another aspect of the invention, a trocar having a varying diameter lumen may be used to allow the angular position of the cannula to be changed. Referring to FIG. 3 a trocar (300), which may facilitate such movement is shown. Trocar (300) generally includes an annular member (302) which forms an annular passageway or lumen (304) which is shown with a varying diameter along a longitudinal direction of the trocar (300). The diameter of the lumen of the embodiment shown increases in both directions away from the central portion (306) of member (302). A portion of the increasing diameter of the lumen is shown in FIG. 4. The size of the lumen depends on the diameter of the cannula to be used therewith. A flange (308) may be provided with the trocar (300) to enhance the securement to the vessel as is conventional to the art. A seal (310) is located within the passageway (304).

FIG. 4 illustrates a front view of the trocar (300). Flange (308) may be attached to the vessel wall (312) with sutures (314) with the seal (310) positioned outside the vessel.

Figure 5:
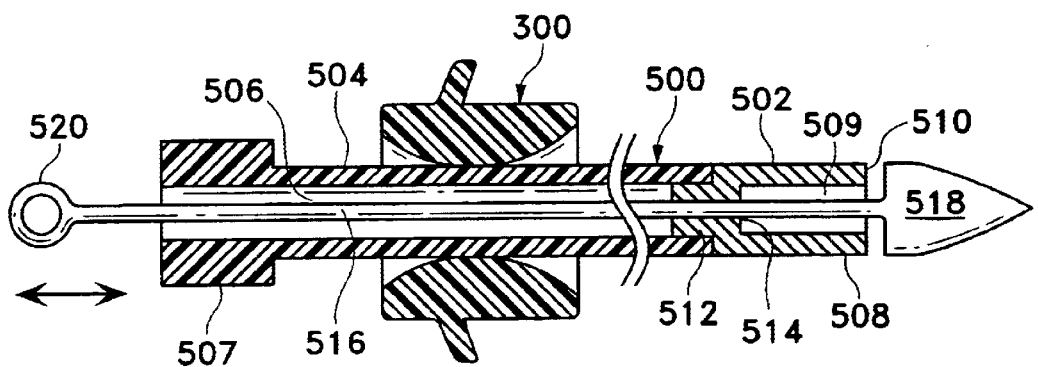
FIG. 5 is a sectional view of another cannula of the present invention disposed in the trocar of FIGS. 2–4.

Referring to FIG. 5, another cannula generally designated with reference numeral (500) is shown positioned within trocar (300) according to another embodiment of the present invention. It should be understood, however, that cannulas (200, 500) can be used alone or with other trocars. Cannula (500) is the same as cannula (200) with the exception that distal portion (502) varies in construction. Proximal portion (504) is the same as proximal portion (204) and may include enlarged diameter portion (507) to act as a stop and prevent entry of the distal end into the trocar as in the case of enlarged diameter portion (207). Distal portion (502) includes a cylindrical portion (508) forming a cavity (509) and having an annular edge (510), that may be squared as shown in the drawing. Adjacent to cylindrical portion (508) is reduced diameter cylindrical portion (512) which is adapted to fit in the lumen (506). Cylindrical portion (512) includes a bore (514) for receiving a rod (516) from which pointed member or conical punch (518) and ring holder (520) extend. The portion of head (518) which is adjacent to edge (510) has an outer diameter greater than the inner diameter of the edge, so that the pierced tissue passes over the head and is pressed against the edge.

According to another aspect of the invention, a surgical fastener or clip cartridge or retainer is provided and may be used with any cannula described above to make an anastomosis. Referring to FIG. 6A, one clip surgical fastener cartridge (600) is shown in accordance with the present invention. Cartridge (600) generally includes a plurality of fasteners (603), which may comprise super-elastic or shape memory material, within a first tubular member or sleeve (604) and a second tubular member or sleeve (602). The tubular members are slidably coupled to one another. One end of the fasteners (603) are biased against the sleeve (602) and the other ends biased against the sleeve (604) by placement between a rod (610) and annular protrusion (612).

FIG. 6B shows a front view of the cartridge of FIG. 6A. Although the cartridge (600) is shown to have 6 fasteners or clips (603), the number of fasteners or clips (603) may vary depending on the particular procedure. FIG. 6A also illustrates rod (610) extending through a proximal end (614) of the cartridge (600). It is also within the scope of this invention to have rod (610) extending through the opposite end of the cartridge retainer (600).

FIG. 6C illustrates a fastener or clip (603) in accordance with the invention. In this figure, the clip is illustrated in an unrestrained shape. The clip (603) is placed in the cartridge (600) and restrained to a second shape as shown in FIG. 6A. One embodiment of a fastener or clip comprises a deformable wire made from a shape memory alloy. A nickel titanium (Nitinol) based alloy may be used, for example. The Nitinol may include additional elements which affect the yield strength or the temperature at which particular pseudoelastic or shape transformation characteristics occur. The transformation temperature may be defined as the temperature at which a shape memory alloy finishes transforming from martensite to austenite upon heating (i.e. $A_f$ temperature). The shape memory alloy preferably exhibits pseudoelastic (e.g., superelastic) behavior when deformed at a temperature slightly above its transformation temperature. At least a portion of the shape memory alloy is converted from its austenitic phase to its martensitic phase when the wire is in its deformed configuration. As the stress is removed, the material undergoes a martensitic to austenitic conversion and springs back to its original undeformed configuration. When the fastener or clip is positioned within the cartridge (600) in its deformed configuration, a stress is present to maintain the fastener or clip tightly against the first and second tubular members described above. In order for the pseudoelastic fastener or clip to retain sufficient compression force in its undeformed configuration, the clip should not be stressed past its yield point in its deformed configuration to allow complete recovery of the wire to its undeformed configuration. It is to be understood that the fastener or clip may comprise other materials as well.

Referring to FIGS. 7–14 a method of preparing an anastomosis in accordance; with the principles of the present invention will be described. In FIG. 7, a trocar (300) is placed into a wall of a vessel. The piercing cannula (200) is passed through the trocar (300) and advanced through another wall portion of the vessel. The distal portion (202) may then be removed from the cannula.

Figure 8:
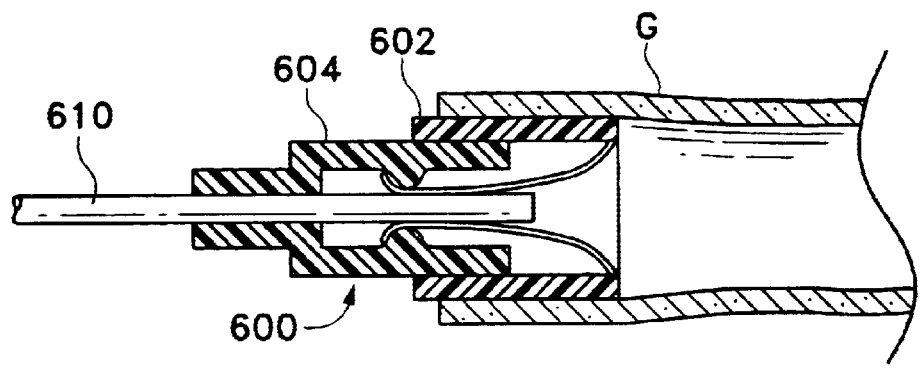
Figure 9:
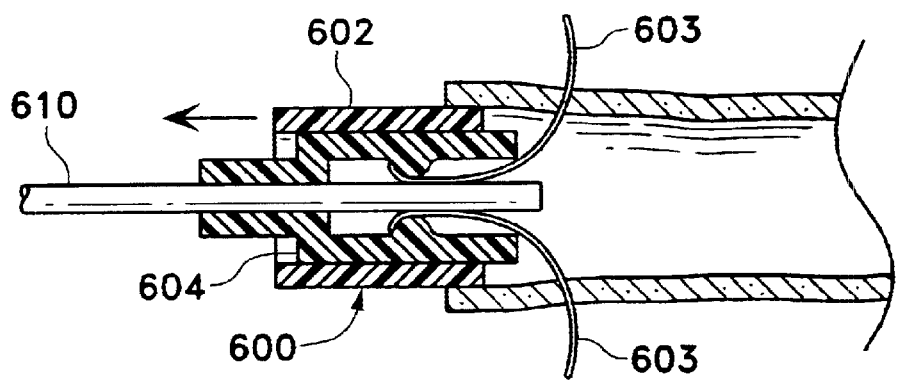
Figure 10:
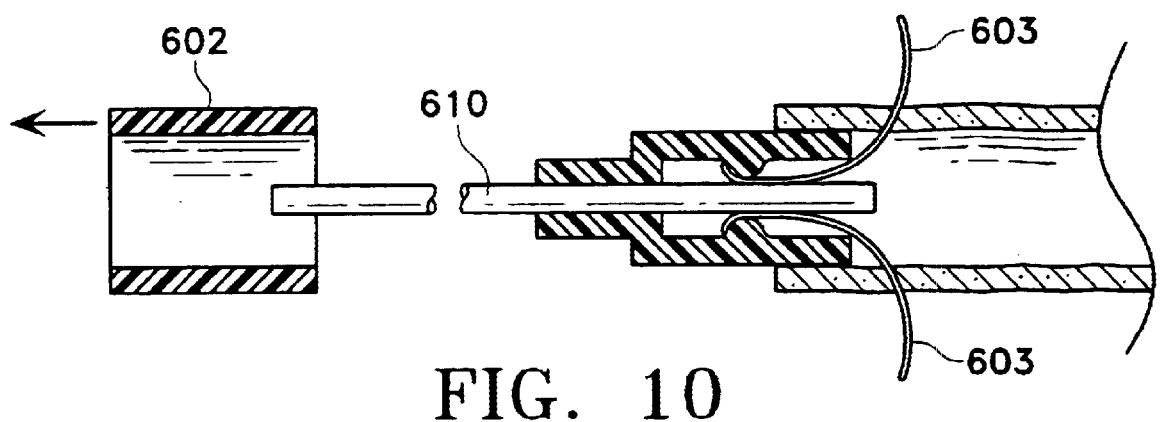
Figure 11:
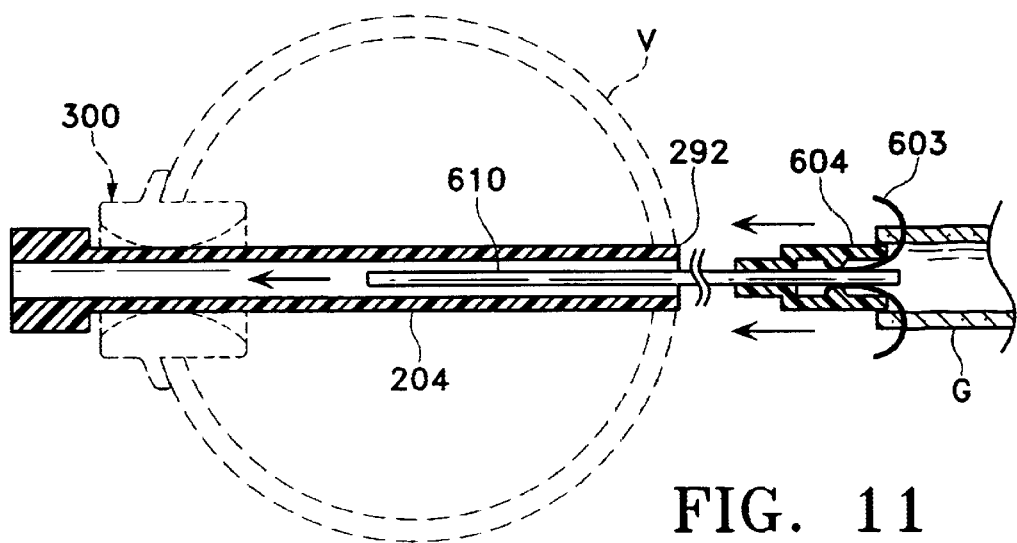
Figure 12:
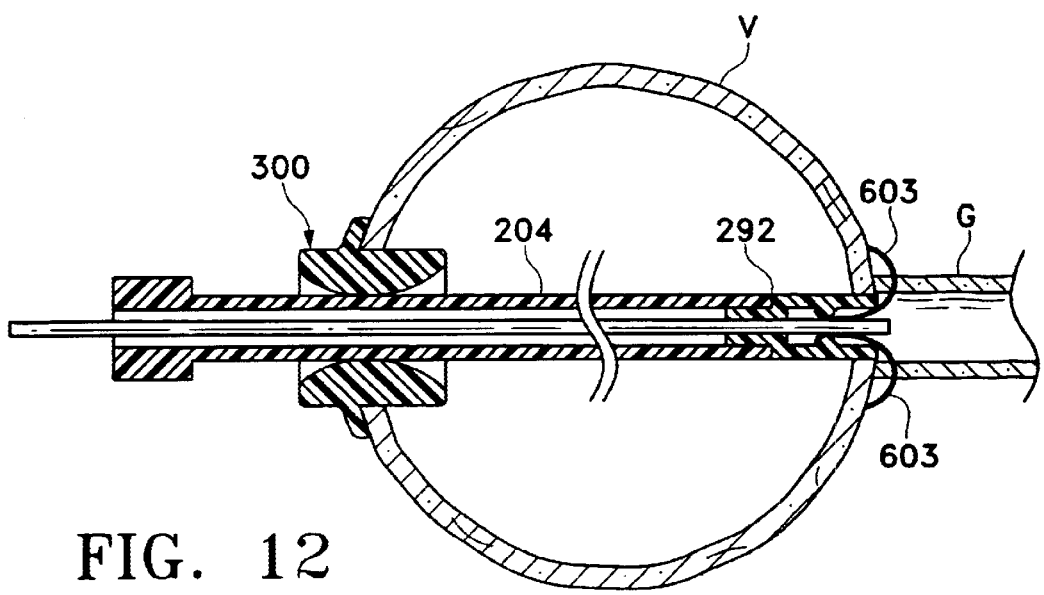
FIG. 12 shows the cartridge in place in the cannula and the released fastener ends engage the vessel.
Figure 13:
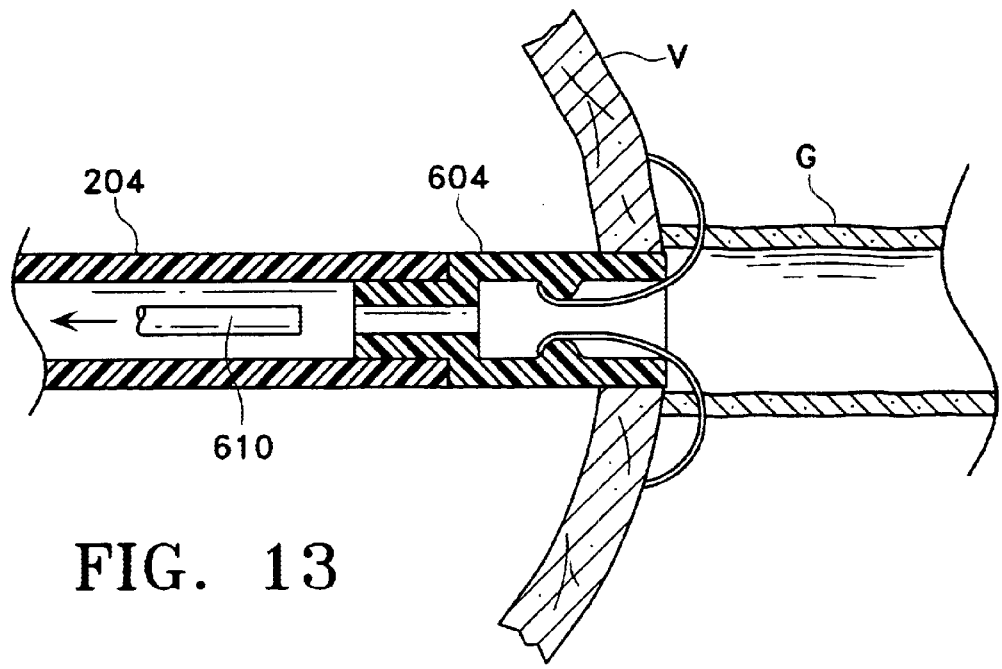
FIG. 13 shows the release of the locking member for the other ends of the fasteners.

Referring to FIGS. 8–10, a tubular graft (G) is slid over first tubular member (602) of cartridge (600). Tubular member (602) then is withdrawn to remove the bias against one end of the fasteners and allow them to penetrate the graft while moving toward a relaxed state (FIG. 9). The first tubular member (602) may then be completely removed (FIG. 10). The second tubular member (604) and graft are then aligned with cannula proximal end portion (204) with rod (610), (FIG. 11) and the second tubular member seated against the cannula proximal portion (292) (FIG. 12).

Figure 14:
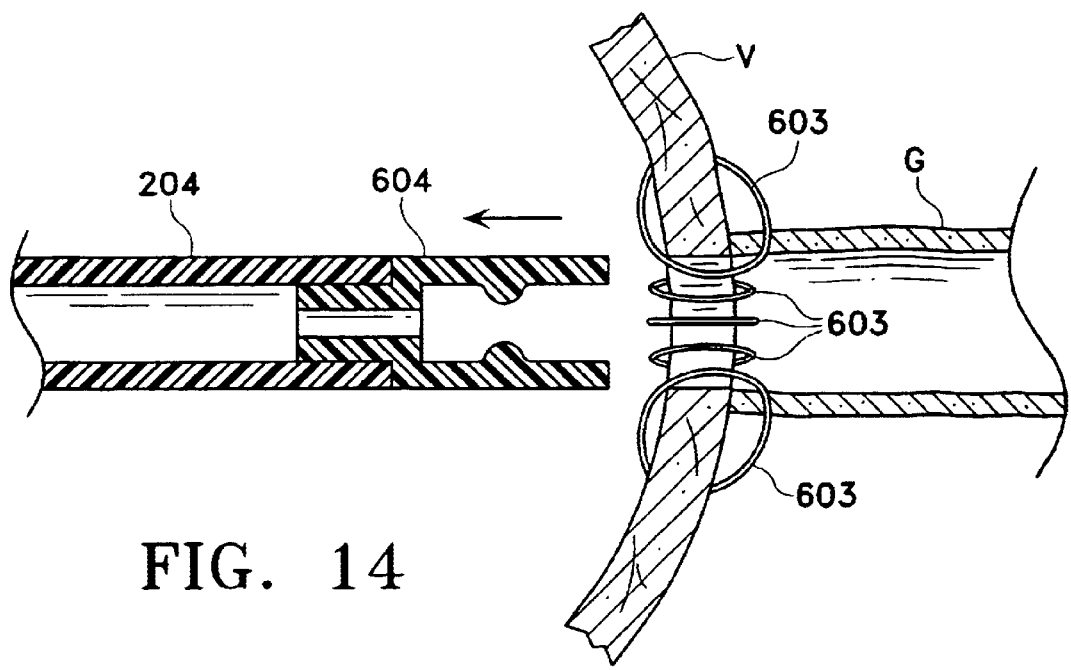
FIG. 14 shows withdrawing the cannula and second tubular member to release the second ends of the fasteners so they may engage the inner wall of the vessel.

Rod (610), which extends through the cannula proximal portion and out from its other end, is pulled to unlock and allow release of other ends of the fasteners (FIG. 13), which are released when cannula proximal portion (204) is withdrawn with second tubular members (604) fractionally fit therein (FIG. 14). Both ends of the clips are then anchored on the inner and outer walls of the vessel, thereby securing the graft thereto.

According to another aspect of the invention as shown in FIGS. 15A–15D, a tubular punch or cutting tool (704) having a distal end (705) adapted to create an opening in a vessel wall (714) is provided. In the example shown, distal end (705) includes a knife edge for cutting though the tissue of the vessel wall. Alternatively, other types of cutting edges could be employed, such as serrated edges, etc, as would be apparent to those of ordinary skill in the art. An anchor member (728) is slidably located within the cutting tool (704). Anchor member (728) has a flexible shaft (707) with a harpoon-like piercing member (708) attached or integral with a distal end thereof. The piercing member (708) is configured to enable relative ease in piercing the vessel wall, while at the same time making it difficult to pull the piercing member back out of the vessel wall. For example, the "harpoon-like" design may include one or more barbs (709) extending from or near the distal end of the shaft (707). It is preferable, when piercing the vessel wall with the "harpoon-like" piercing member (708) to rotate the shaft (707) somewhat after the piercing member (708) has passed through the vessel wall, to make it more difficult for the barbs (709) to find their way into a return pathway which would be the same pathway through which they entered. Alternatively, the piercing member may be configured to be expandable after it passes through the vessel wall, e.g., the piercing member may have an "umbrella-like" actuation (not shown), in which struts expand so as to form an area much larger than the original outside diameter of the piercing member, and approaching an area equal to the area of tissue to be excised. Once opened, the umbrella like member would then be pulled flush against the inner wall of the vessel in preparation for clamping with a disk (720) (described below).

The shaft (707) may be formed from medically acceptable polymers, stainless steel or Nitinol, for example and is flexible, yet stiff enough to have sufficient column strength to push the piercing member through the vessel wall. For normal CABG surgery, the tubular punch (704) preferably has an inner diameter between about 3.0–6.0 mm and a wall thickness between about 0.150–0.200 mm.

Figure 15B:
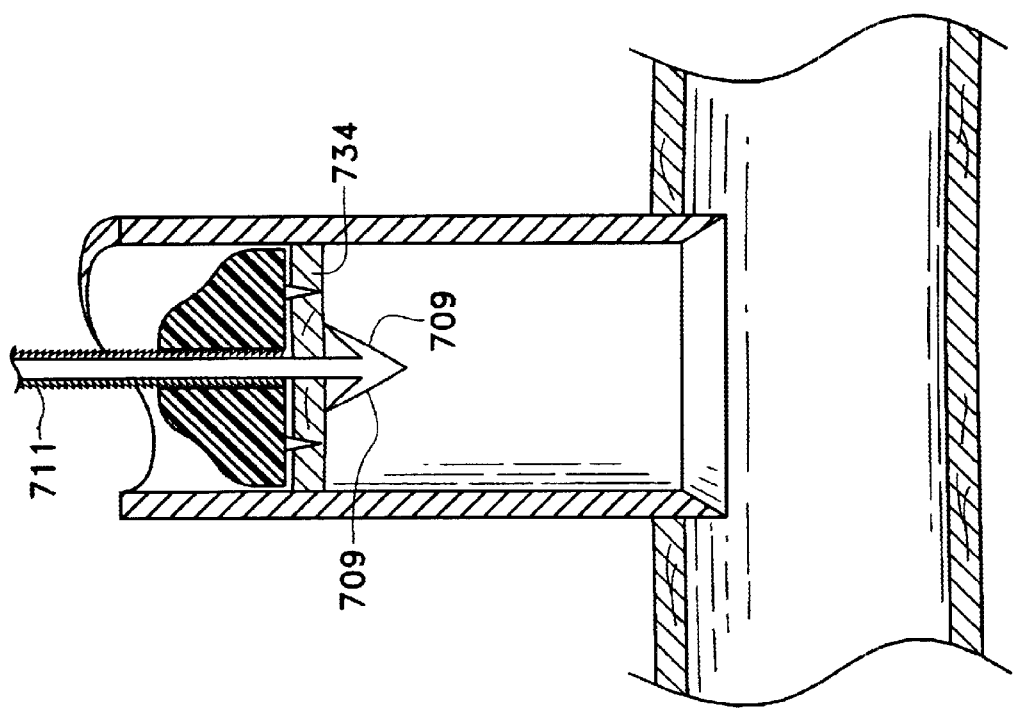
FIG. 15B is a sectional view of the device of FIG. 15A after an opening is created in the vessel wall by the punch and the tissue cut is being retrieved.
Figure 15A:
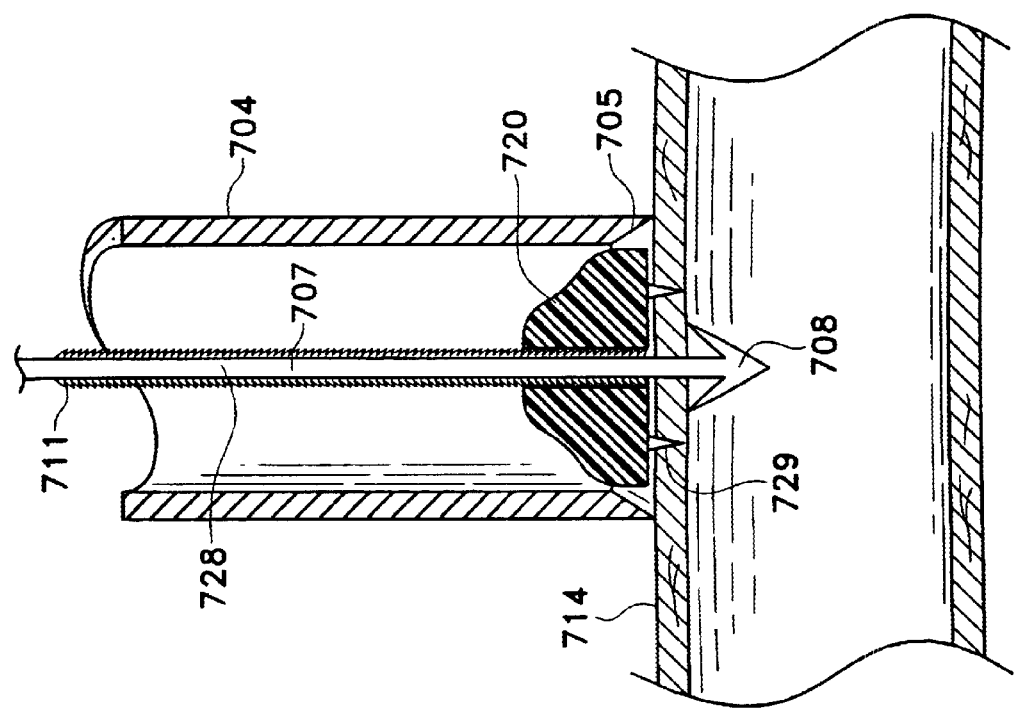
FIG. 15A is a sectional view of another proximal anastomosis device with a punch, an anchor member and a centering disk.
Figure 15D:
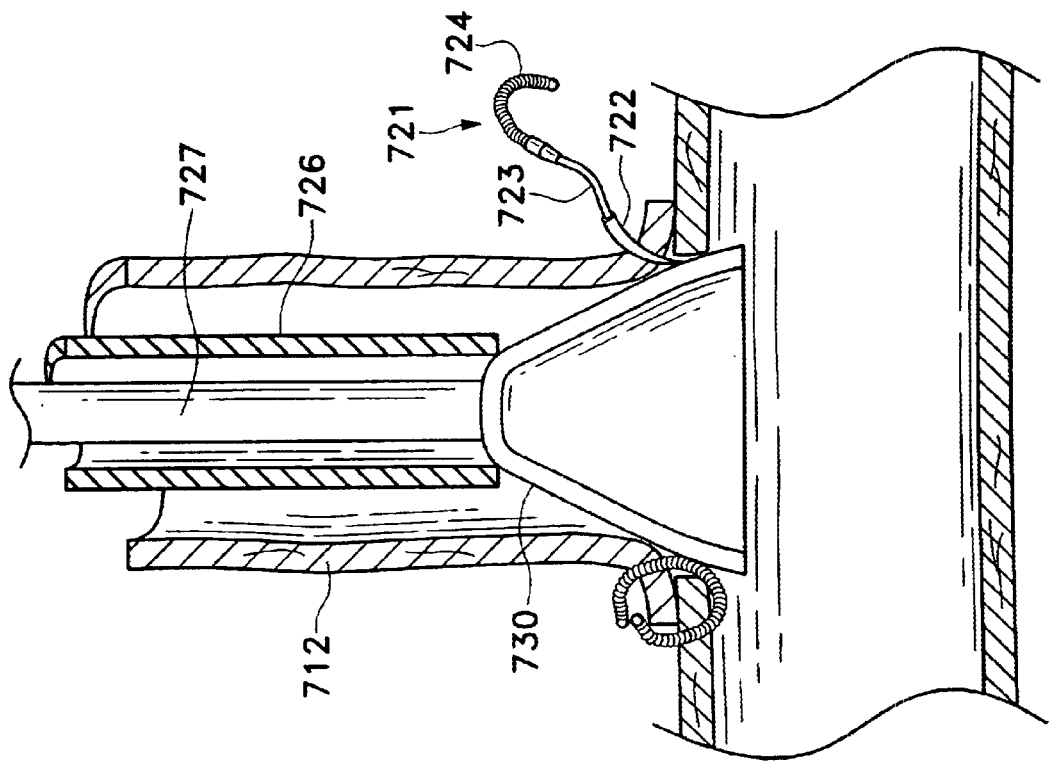
FIG. 15D is a sectional view of the device of FIG. 15A with the punch retrieved and a graft slid over the radially expandable member to be attached to the vessel by a plurality of self-closing fasteners.
Figure 15C:
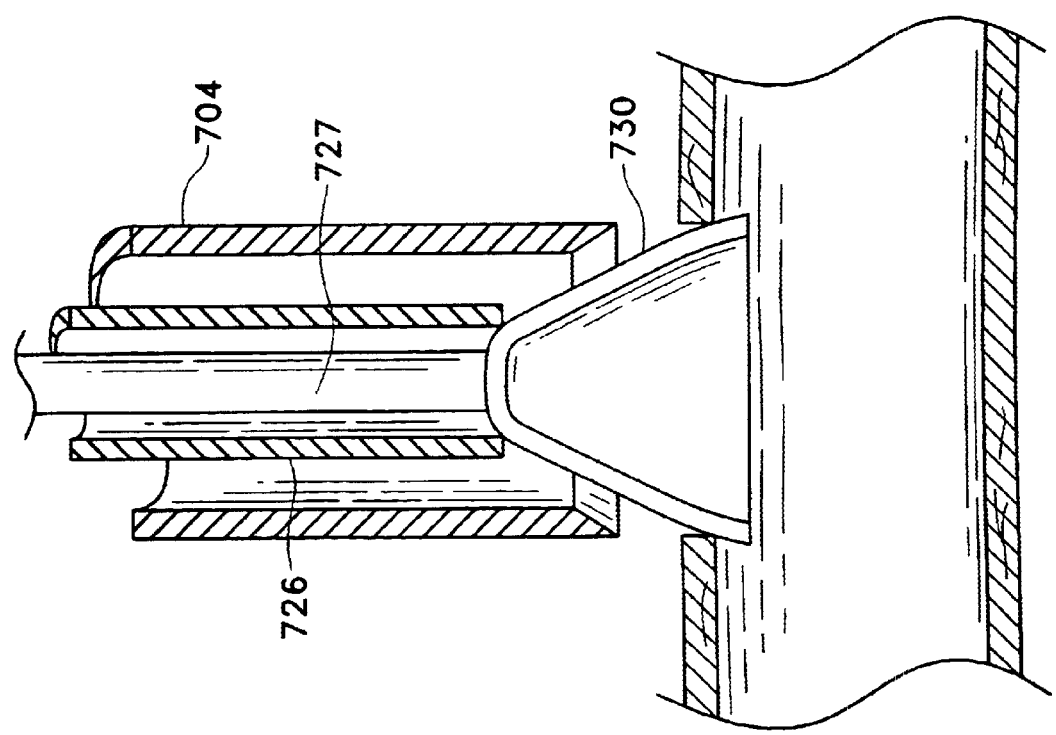
FIG. 15C is a sectional view of the device of FIG. 15A with an occlusion member comprising two coaxial cylinders and a radially expandable member attached to the distal end of the inner cylinder.
Figure 15F:
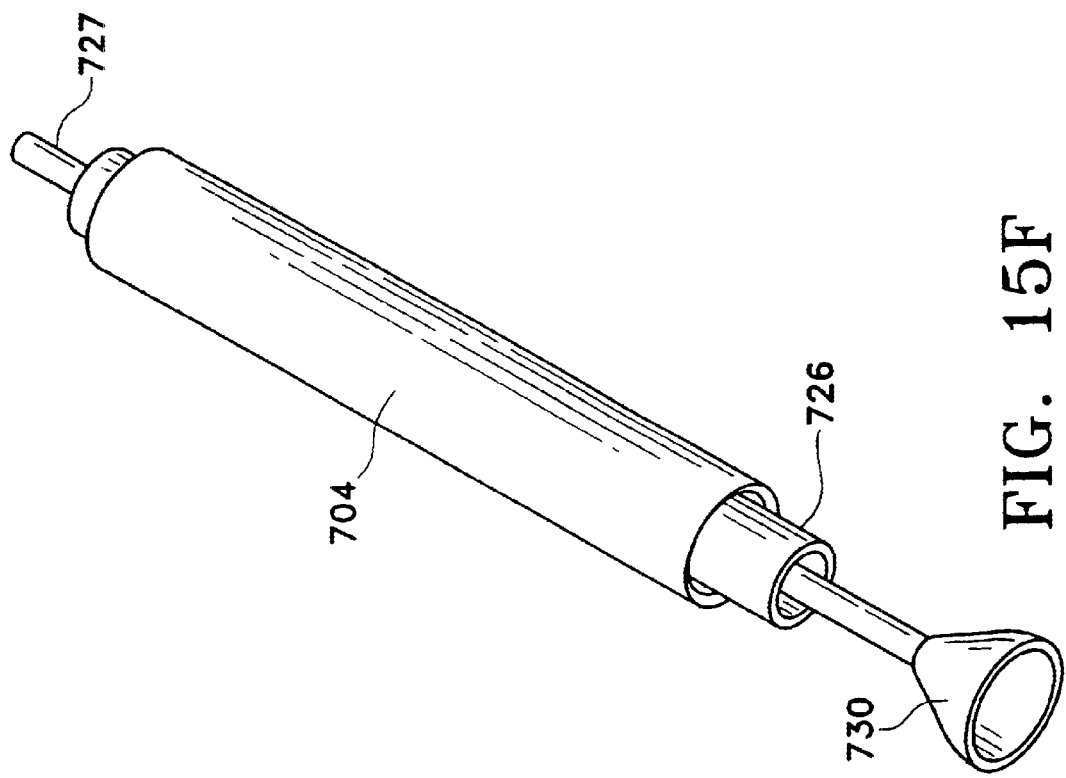
FIG. 15F is a perspective view of the device shown in FIG. 15C.
Figure 15E:
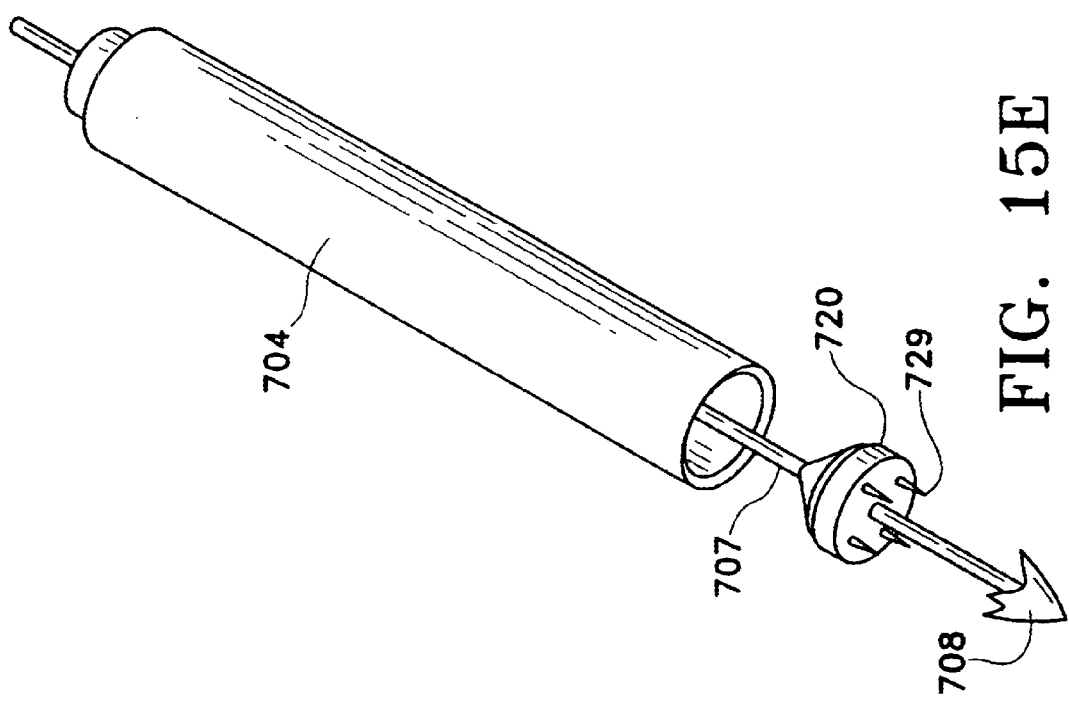
FIG. 15E is a perspective view of the device of FIG. 15A with a punch, an anchor member and a centering disk.

Whether barbed, umbrella-like, or some other expanding configuration, the piercing member (708) is tapered, and preferably pointed, in its "pre-entry" configuration, in order to pierce the vessel wall (FIG. 15E). The piercing member may be affixed to the flexible shaft (707) by glue or equivalent fixation methods, or can be an integral part of the shaft itself.

Once piercing member (708) has pierced the wall of vessel (714) and the operator has either rotated the shaft (707) (barbed configuration) or expanded the piercing member and pulled it back against the inner wall of the vessel (714) (umbrella-like or other expanding configuration), a generally circular centering disk (720) may be slid down along the flexible shaft (707), as shown in FIG. 15A. The shaft (707) may be provided with serrations (711) similar to a tie lock, so that once the disk (720) passes over the serrations, it is prevented or locked from being slid back in the opposite direction. In this way, the disk (720) is slid down into position and locked to sandwich the tissue of the vessel wall and no backsliding of the disk will occur. Thus a firm fixation of the tissue is made for an accurate and cleaner cut. Other locking arrangements may be used such as following the disk with a friction tubing (not shown) which is difficult to remove from the shaft (707) and forms a friction stop against which the disk (720) abuts, thereby preventing back sliding or movement of the disk. Other friction or locking arrangements could be substituted to perform the same function, as would be readily apparent to those of ordinary skill in the art.

The centering disk (720) may also function to keep the flexible shaft (707) at the center of the tubular punch (704) and coordinate with the piercing member to retain and retrieve the tissue cut (734), as shown in FIG. 15B. To that end, the centering disk may have one or more spikes (729) extending out from its surface and adapted to partially pierce or at least frictionally engage the outer wall of the vessel, in order to assist the fixation of the tissue section to be cut. The lengths of the spikes are preferably less than about 5 mm, so as to not completely pierce through the vessel wall and possibly cause blood loss therefrom. Further, the sizing of the spikes are such that they are not long enough to dislodge plaque, as some lengths may not completely pierce the vessel wall, but would extend far enough into the wall to dislodge plaque, thereby raising the risk of stroke, etc., as described previously. The spikes are preferably formed of stainless steel or Nitinol. Although the disk (720) may be formed of Nitinol or stainless steel and the spikes may then be integrally formed therewith, the disk is preferably formed from a polymer such as ABS or polyurethane or other medically acceptable polymers suitable for this purpose, in which case the spikes may be glued, molded in, threaded or otherwise affixed to the disk.

With regard to the operation procedure, after the physician pushes the shaft to insert the piercing member (708) through the vessel wall, and after the piercing member is deployed (when using an umbrella-type actuator), or the barb type piercing member has been rotated, he or she will twist the punch (704) to create an opening in the vessel wall. Thereafter, the severed tissue (734) is held in place between the piercing member (708) and the centering disk (720), and retrieved through the inner lumen of the punch.

After the retrieval of the severed tissue (734), an occlusion device is inserted in order to prevent blood loss through the opening in the vessel wall. The occlusion device comprises two coaxial cylinders (726, 727) as shown in FIG. 15C. The inner cylinder (727), which can be either solid or hollow, is slidably located within the outer cylinder (726). A radially expandable member (730) is attached to an distal end of the inner cylinder (727) and is configured to substantially occlude the opening of the vessel wall once it is inserted into the vessel and extended outside the outer cylinder (726). The radially expandable member 730 is shown in its fully expanded state in FIG. 15F.

For normal CABG surgery, the outer diameters of the inner and outer cylinders are less than about 3 mm and about 6 mm respectively. Preferably, the inner cylinder comprises polymer (polethylenes, polyurethanes, polyamides, polypropylenes) or other acceptable preferred materials, or stainless steel) materials such that it is flexible enough to allow side-to-side movement, and yet has sufficient column strength for the physician to push or pull it through.

Disk (720) may have a friction feature or ratchet (e.g., like a tie wrap) or some type of self-locking mechanism against shaft (707) to frictionally engage or otherwise resist backwards movement of the disk along the shaft. Thus, once the disk is engaged against the tissue of the vessel wall, it sandwiches the tissue cut (734), in cooperation with the piercing member on the opposite side of the vessel wall.

Figure 16F:
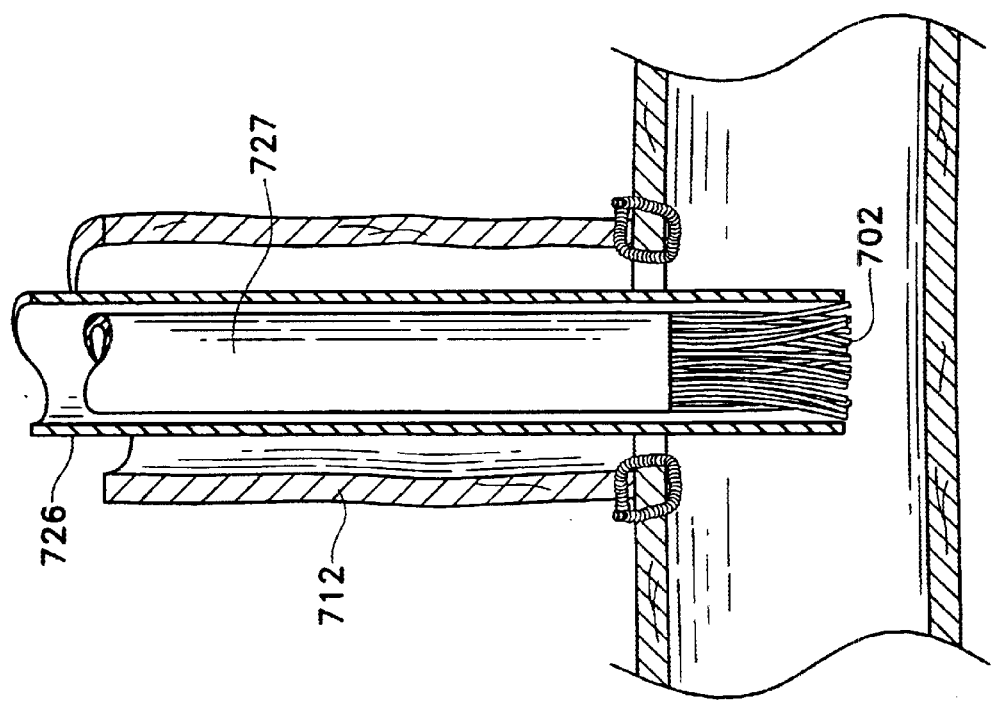
FIG. 16F is a sectional view of the device of FIG. 16A with the outer cylinder slid down over the bristles after an anastomosis has been formed.
Figure 16E:
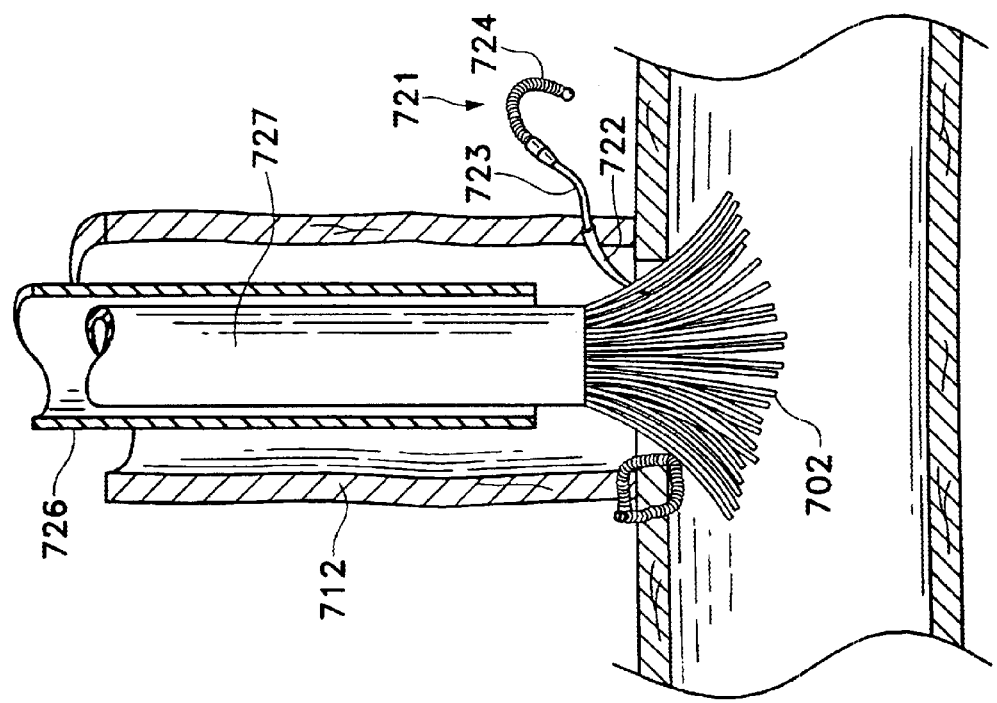
FIG. 16E is a partial sectional view of the device of FIG. 16A with the punch withdrawn, the occlusion device in place with the bristles expanded or deployed, and a plurality of fasteners inserted to attach a graft to the vessel wall.

According to one embodiment of the occlusion device illustrated in FIG. 16A, the radially expandable member of the occlusion device comprises a plurality of bristles (702) attached to the distal end of the inner cylinder (727). The bristles (702) have memory shapes that flare outwardly from the distal end of the inner cylinder (727) once the restraint upon the bristles is removed, in order to create a hemostasis area at the opening of the vessel wall as further described below.

Referring to FIG. 16A, after the punch (704) creates an opening in the vessel wall (714) and the severed tissue is retrieved by the anchor member (728) along with the centering disk (720), the inner cylinder (727) is slid down along with the outer cylinder (726) towards the vessel, with the bristles (702) at its end restrained from expanding by the outer cylinder. After the bristles are at least substantially inserted within the vessel (FIG. 16B), the punch (704) and outer cylinder (726) are pulled back from the vessel and withdrawn. As the restraint is removed, the bristles (702) turn into their memory shape and expand outwardly to form an area of hemostasis at the opening of the vessel wall. Therefore, the vessel does not need to be clamped while an anastomosis is being performed adjacent to the hemostasis area and blood can continue to flow within the vessel.

As shown in FIG. 16C, the bristles (702) can be constrained to the inner cylinder through a retaining ring (709). The retaining ring (709), binding around a bundle of bristles, is itself attached to the distal end of the inner cylinder (727) by glue or other conventional mechanical fixing approaches known in the art. Alternatively, the bristles are glued to the inside wall of the inner cylinder (727) as shown in FIG. 16D.

Once an area of hemostasis is created with the bristles (702) in place, a graft (712) is brought down over the outer cylinder (726) in place to form an anastomosis (F 16E). A plurality of self-closing fasteners (721), each of which includes a memory coil (724), a deformable wire (not shown, as it is surrounded by memory coil (724)) made of a shape Memory alloy, a suture (723) and a needle (722), are used to attach the graft to the vessel. Such self-closing fasteners are described in detail in copending and commonly assigned U.S. application Ser. No. 09/090,305 filed Jun. 3, 1998; WO 99/62406; WO 99/62409; and a copending and commonly assigned application entitled "Multiple Bias Surgical Fastener" (Attorney's Docket No. 388402001700) which was filed concurrently herewith and assigned U.S. application Ser. No. 09/541,399. Each of the aforementioned documents are hereby incorporated by reference herein in their entireties. Such fasteners can be manipulated by a pair of conventional tweezers known in the art. For grafts and vessels with diameters within the range of 2.5 mm and 6 mm, it is preferred that twelve fasteners be put in before the bristles are retrieved. The same types of fasteners may be used in closing the anastomosis with the device described above with regard to FIGS. 15A–15E.

Figure 16G:
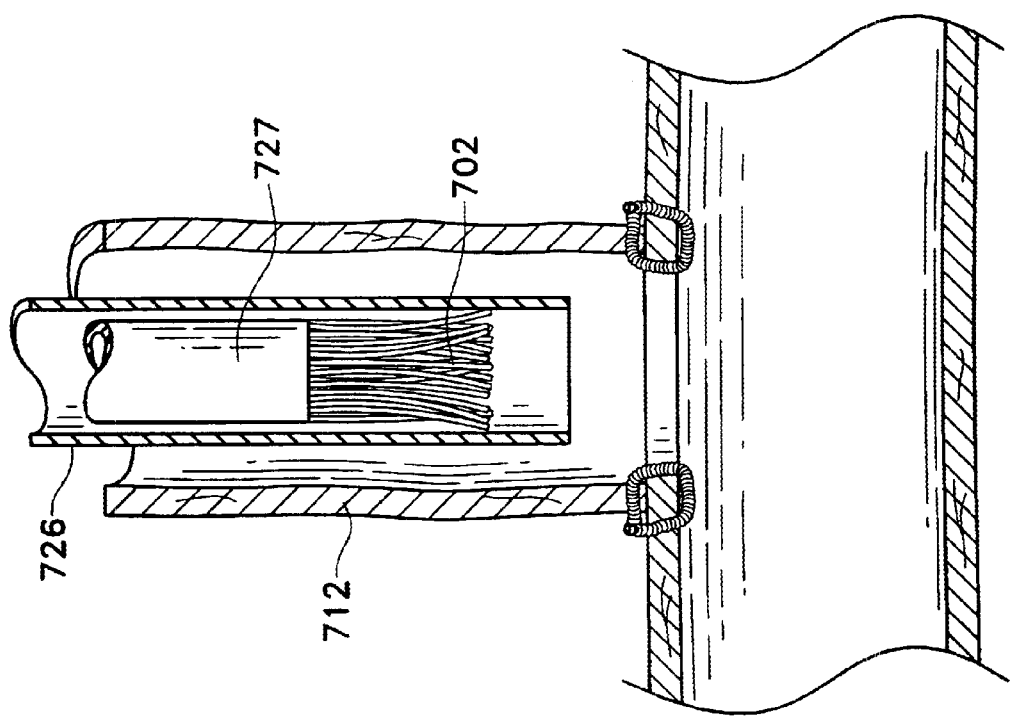
FIG. 16G is a sectional view of the device of FIG. 16A with the occlusion device being withdrawn.

After the anastomosis is formed, the outer cylinder (726) is brought down over the bristles (702) to force them back into a compressed state within the outer cylinder (FIG. 16F) and therefore, dissolving the temporary seal formed at the opening in the vessel wall. Finally, the inner cylinder (727) is retrieved through the outer cylinder (726) along with the bristles (FIG. 16G).

One embodiment of the bristles (702) comprises deformable wires made from a shape memory alloy. A nickel titanium (Nitinol) based alloy may be used, for example. The Nitinol may include additional elements which affect the yield strength or the temperature at which particular pseudoelastic or shape transformation characteristics occur. The shape memory alloy preferably exhibits pseudoelastic (e.g., superelastic) behavior when deformed at a temperature slightly above its transformation temperature. At least a portion of the shape memory alloy is converted from its austenitic phase to its martensitic phase when the wire is in its deformed configuration. As the stress is removed, the material undergoes a martensitic to austenitic conversion and springs back to its original undeformed configuration.

When the bristles are positioned within the outer cylinder (726) in their deformed configuration, a stress is present to maintain the bristles tightly therein. In order for the pseudoelastic bristles to retain sufficient compression force in their undeformed configuration, the bristles should not be stressed past their yield point in their deformed configuration to allow complete recovery of the bristles to their undeformed configuration. It is to be understood that the bristles may comprise other materials as well. Depending upon the size of the vessel and the graft, the length of the bristles extending from the distal end of the inner cylinder (727) cam range from about 5 mm to about 20 mm.

According to another embodiment of the occlusion device as shown in FIG. 17A, the radially expandable member comprises an inflatable membrane (800) attached to the distal end of the inner cylinder (727). The inner cylinder has an internal lumen so that air can be pumped into the membrane (800) therethrough.

After the opening in the vessel wall is created, the anchor member (708) and the optional centering disk (720) are withdrawn from the vessel along with the severed tissue. The physician then inserts through the punch the occlusion member which comprises two generally coaxial cylinders (726, 727) and the membrane (800) in a deflated state. When the membrane (800) is at least substantially within the vessel (FIG. 17B), the punch (704) and the outer cylinder (726) are withdrawn and the membrane is inflated to occlude the opening and form an area of hemostasis.

Each of the fasteners used with this embodiment of the occlusion device has two needles (722, 725), one at each end. The fasteners are removably attached to the membrane and inserted into the vessel together with the membrane. The fasteners (721) can be glued to the membrane or attached to the membrane through a mechanical fitting such as a sliding or snap fit made of an acceptable material which may be mounted or insert molded into the membrane.

Figure 17C:
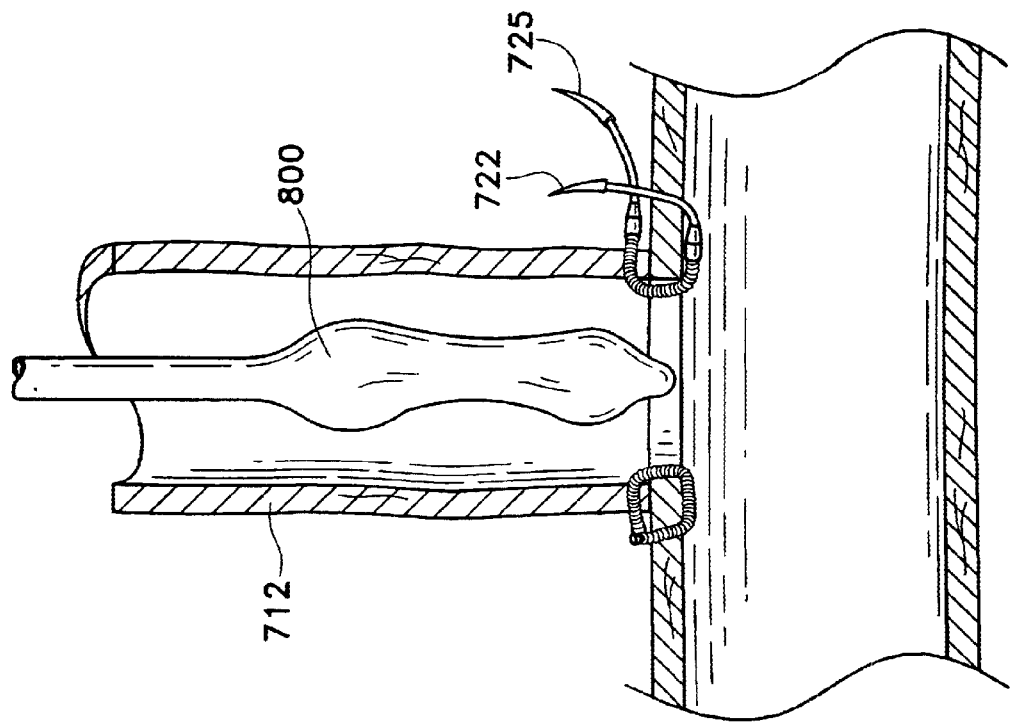
FIG. 17C is a sectional view of the device of FIG. 17A with the fasteners piercing through a graft to attach the graft to the vessel.
Figure 17D:
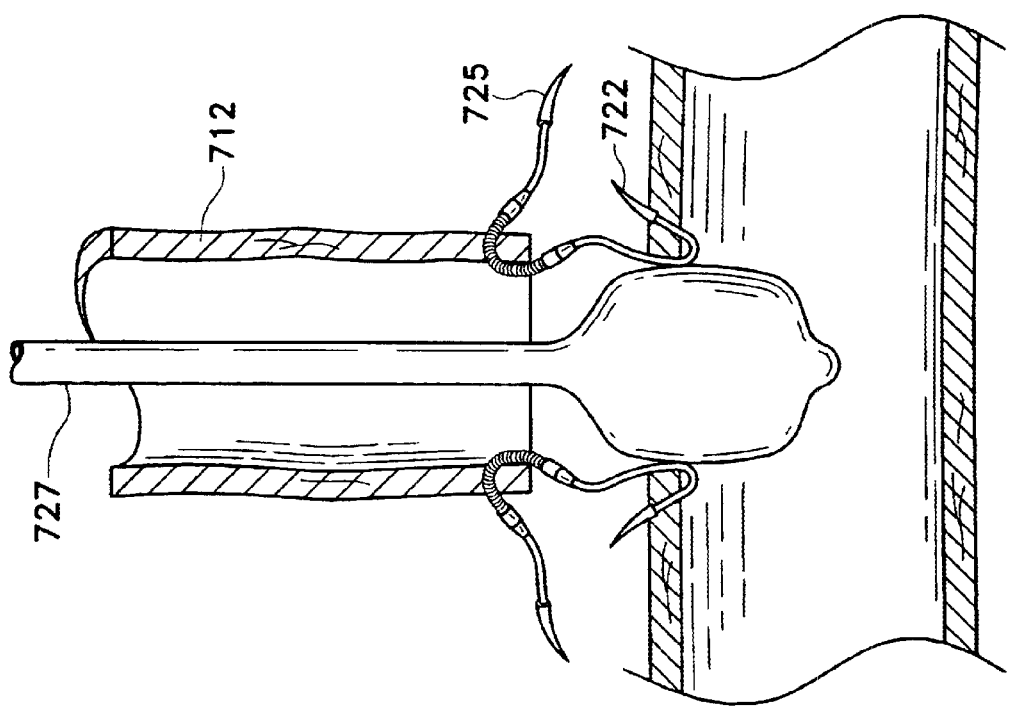
FIG. 17D is a sectional view of the device of FIG. 17A with the membrane deflated after the anastomosis is formed.

Each fastener is so removably attached to the membrane that only one needle (722) remains inside the vessel after the membrane (800) is inflated. As the membrane is slightly pulled back by the physician, the needle inside the vessel pierces through the vessel wall. Such needle (722) is then pulled completely out of the vessel. As the needle (722) is being so pulled, it causes the fastener to separate from the membrane and moves the suture (723) and the memory coil (721) along with it (FIGS. 17C). Meanwhile, a graft (712) is brought down to be attached to the vessel. The other needle (725) that has not been inserted into the vessel is then manipulated to pierce through the graft. Such needle (725) leads the suture (723) and the memory coil (721) through the graft. After both ends of the memory coil are outside the graft and the vessel, the memory coil self closes upon a release of the locking mechanism and both the suture (723) and the needles (722, 725) are released and removed (FIG. 17D). When sufficient number of fasteners are securely placed between the graft and the vessel, an anastomosis is successfully performed. The membrane is then deflated and moved out along with the cylinder (727) through the graft.

FIGS. 17E–17K are detailed drawings of a fastener (721) and portions thereof, which may be used in connecting the graft (712) to the vessel, as described above and below. Although described in conjunction with the embodiment of FIG. 17A, it is noted that fasteners of this type may be used with any of the other embodiments of the present invention described herein.

Figure 17E:
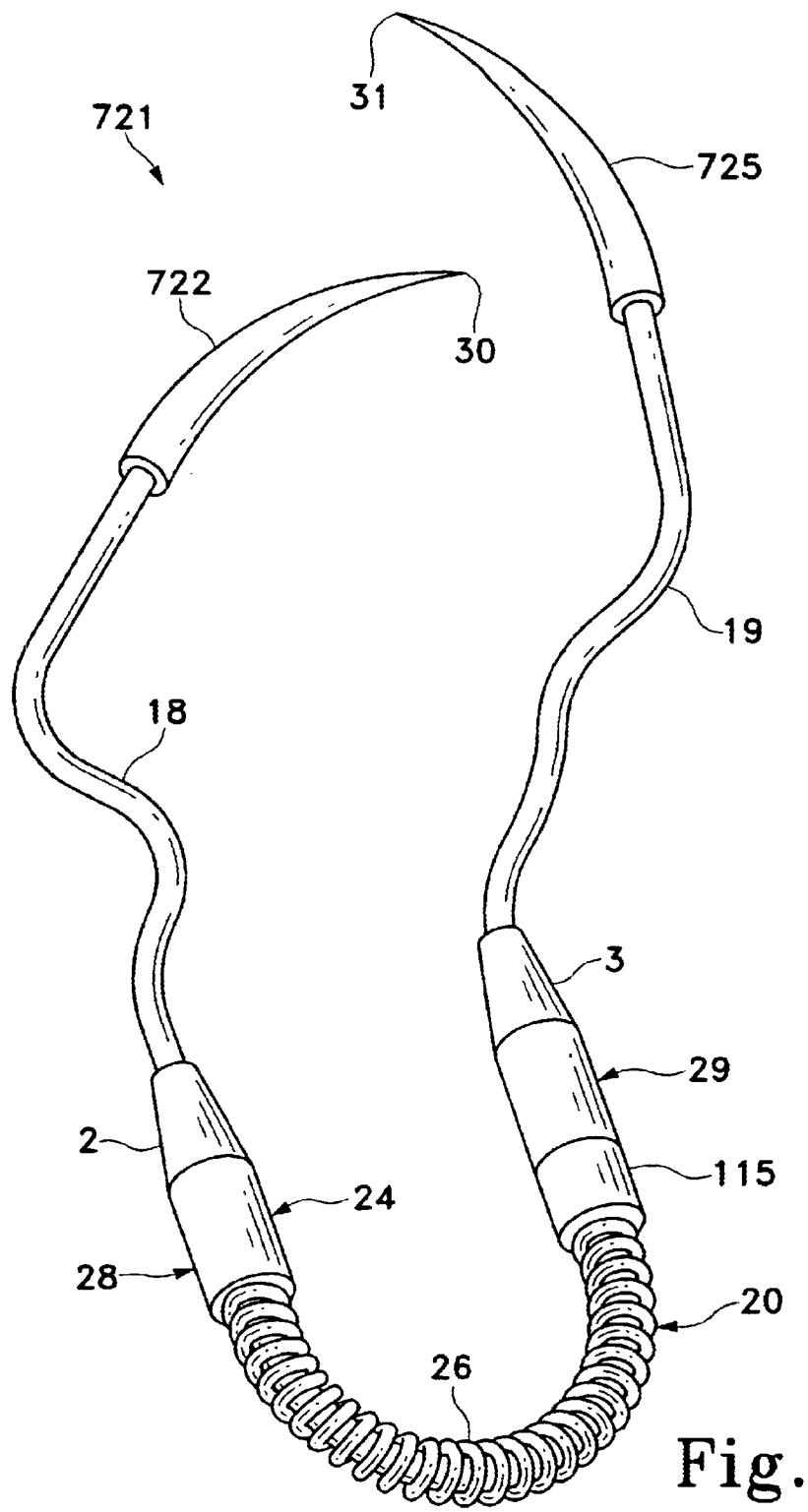

Referring to FIG. 17E, a tissue connector assembly (721) having multiple piercing members is shown. In a preferred embodiment, two piercing members (722) and (725), each of which may comprise a needle, are releasably coupled to a fastener. The coupling between the flexible member (18, 19), and thus, the piercing member (722, 725) and the fastener (721) may be constructed to actuate closure of the fastener (721) upon release of the flexible member (18, 19) (or piercing member) (722, 725). For example, the coupling may hold a compression spring (26) (which is positioned around a fastener) in a compressed state to brace the fastener open and releasably lock or secure the fastener to the flexible member (or piercing member).

As shown in FIG. 17E, a tissue connector assembly (721) which generally comprises tissue piercing or penetrating members (722) and (725), flexible members (18) and (19), and a fastener (20) (e.g., a surgical slip) is shown. A restraining device, generally indicated at (24) and comprising a spring (or coil) (26) and a locking device (or coupling member) generally indicated at (28) and (29), are connected to fastener (20) for holding the fastener in a deformed or open configuration as will be further described below. Penetrating or piercing member (725) may be made in accordance with the description provided above in connection with penetrating member (721), and, thus may, for example, be in the form of a needle (such as a 7-0 or 8-0 needle) having a sharp pointed tip (31) at its distal end for penetrating tissue. Members (722) and (725) are preferably the same but may differ from one another. Flexible members (18) and (19) and tapered portions (2) and (3) also may have the same construction.

Figure 17F:
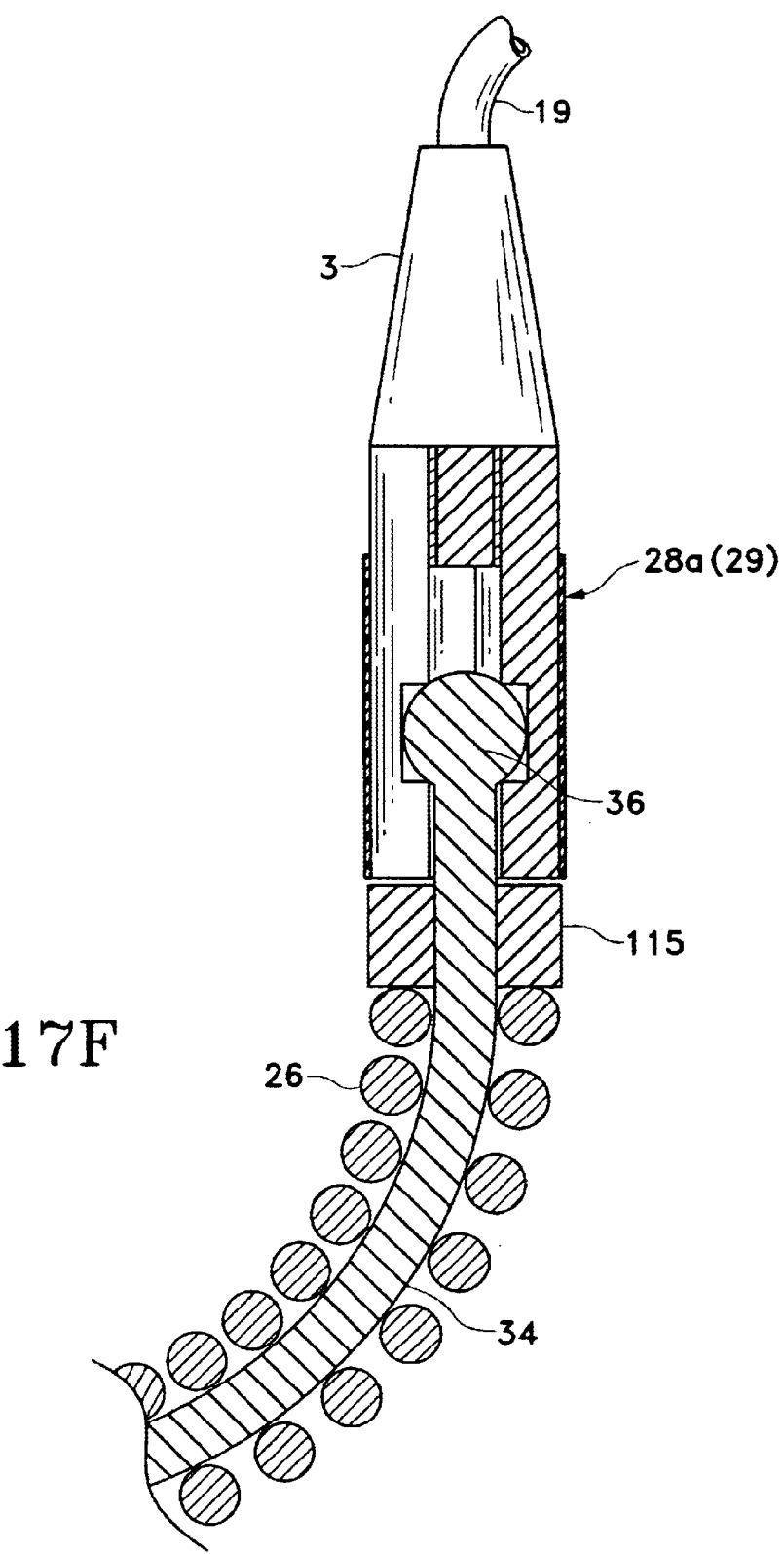

Referring to FIG. 17F, a release mechanism (28a) also may be used as release mechanism (29) to releasably couple the other end of the fastener to another flexible member such as flexible member (19), which in turn, in coupled to a needle such as needle (725) as shown in FIG. 17E. In this arrangement, a member or stopper (115), which may be annular, is secured to the other end of the fastener or wire (34) to prevent enlarged portion (36) from passing through the compression spring upon release from release mechanism (28a).

Figures 17G, 17H:
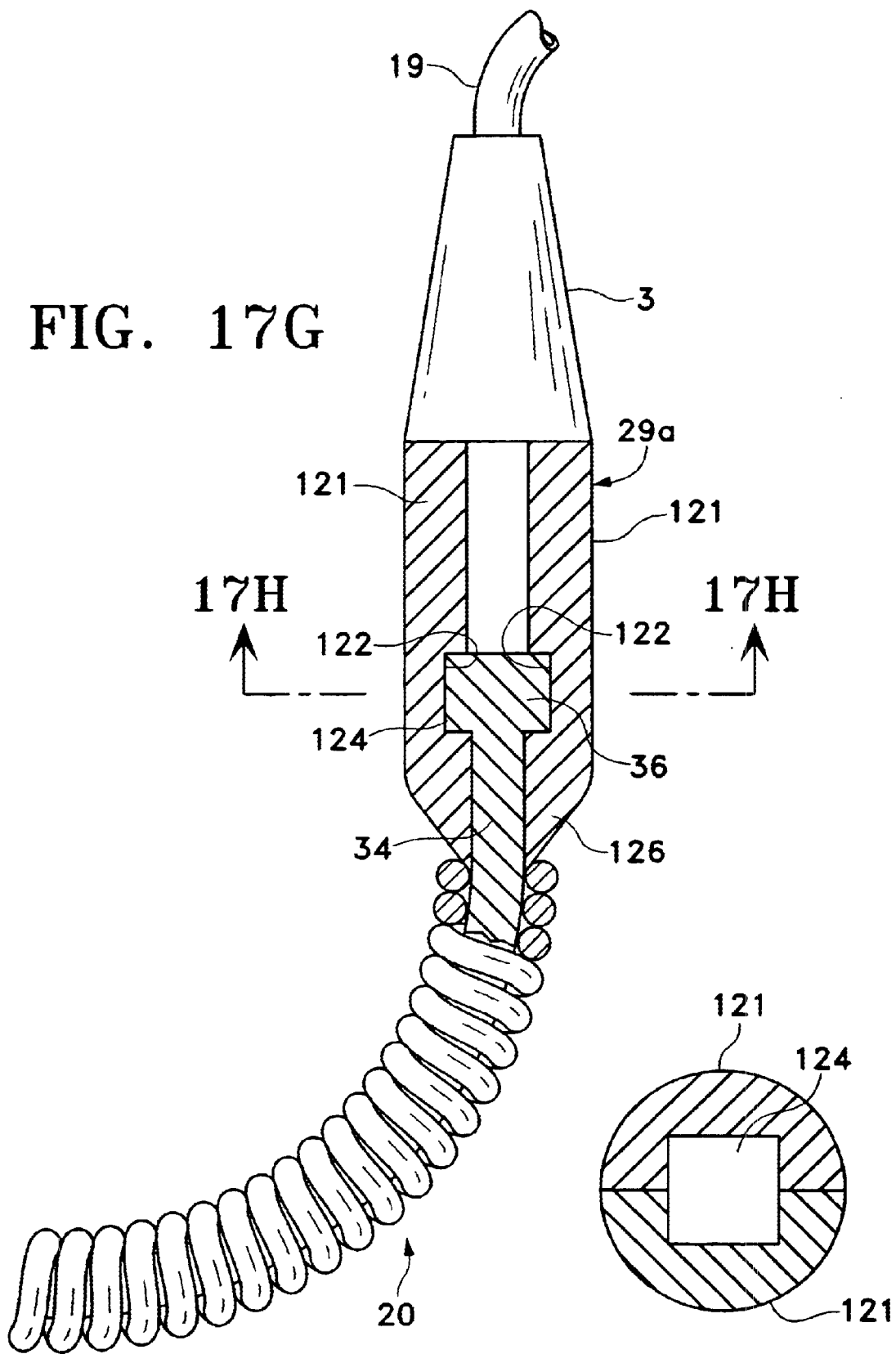

FIGS. 17G and 17H illustrate a synchronized fastener release system. One release mechanism may correspond to mechanism (28a). At the other end of the fastener or wire (34), a release mechanism which responds to the compressive state of coil (26) and releases the fastener or wire (34) upon release of compressive forces on the coil is shown and generally designated with reference numeral (29a). Referring to FIGS. 17G and 17H, release mechanism (29a) comprises two members (121), each having a recess (122) formed therein and arranged to form chamber (124) when members (121) are aligned as shown in FIG. 17G. Recesses (122) are configured to retain enlarged portions (36), which are shown with a cylindrical configuration, but may have a spherical or other suitable shape for operatively associating with a suitably configured chamber. Further, members (121) may have semicircular transverse cross sections or some other combination of transverse shapes that can collectively provide the desired chamber to retain enlarged portion (36). The number of members (121) also may vary as would be apparent to one of ordinary skill.

Release mechanism members (121) have tapered ends (126), which are configured for positioning between coil (26) and fastener wire (34) as shown in FIG. 17G. When tapered ends (126) are so positioned and coil (26) is in a compressed state, coil (26) holds tapered ends (126), which are normally biased away from each other, sufficiently together to retain enlarged portion (36) within chamber (124). When release mechanism (28a) is actuated (e.g., radially compressed) to release enlarged portion (36) of fastener wire (34), coil (26) assumes its relaxed state, thereby releasing tapered ends (126) of release mechanism. (29a) from the coil and allowing the tapered ends to radially expand and release enlarged portion (36) of fastener wire (34). Accordingly, both needles and flexible member may be decoupled from the fastener when released mechanism (28a) is actuated. Further description of the release mechanisms described above are included in copending, commonly assigned application Ser. No. 09/259,705 and 09/260,623 entitled "Tissue Connector Apparatus with Cable Release" and "Tissue Connector Apparatus and Methods", respectively, both of which were filed on Mar. 1, 1999, and both of which are incorporated by reference thereto, herein in their entireties. Additionally, copending and commonly assigned application entitled "Multiple Bias Surgical Fastener" (Attorney's Docket No. 388402001700, which was filed concurrently herewith and assigned U.S. application Ser. No. 09/541,399, and which was incorporated by reference above) describes additional double needle fasteners, including, for example, a multiple bias fastener having double needles, which may be used in the present examples.

FIGS. 17I–17K show another synchronized fastener system which is the same as the system described with reference to FIGS. 17F–17H with the exception of release mechanism (29b) and the cooperating portion of the fastener or wire (34) being substituted for release mechanism (29a). In this embodiment, a member or stopper (115), which may be annular, is slidably coupled to fastener wire (34). Member (115) is configured to resist passage of coil (26) thereover. Accordingly, member (115) may have an outer diameter slightly greater than at least the portion of the coil adjacent thereto. A tapered or frustoconical member (3') is secured to an end of fastener wire (34), which need not include an enlarged portion. Member (3') is the same as member (3) with the exception that member (3') has a channel (134) for receiving flexible member or suture (19), as shown in FIGS. 17I and K. Channel. (134) extends radially outward from bore (132), which is formed through member (3'), for receiving the fastener or wire (34).

Flexible member (19) is threaded through channel (134) and between tapered member (3') and annular member (115). When coil (26) is in a compressed state as shown in FIG. 17I, the coil urges member (115) toward tapered member (3') and compresses flexible member (19) therebetween. In this manner, flexible member (19) is secured to the fastener or wire (34). When release mechanism (28c) is actuated (e.g., radially compressed) to release enlarged portion (38) of the fastener or wire (34), coil (26) assumes its relaxed state so that annular member (115) may slide away from tapered member (3') and release flexible member (19). Accordingly, both needles and flexible members may be removed from the fastener when release mechanism (28c) is actuated. Although a metal flexible member may be used, a polymeric flexible member may be preferred.

As shown in FIG. 17I, for example, coil (26) comprises a helical wire forming a plurality of loops which define a longitudinal opening for receiving a shape memory alloy wire (34). Coil (26) may be formed from a platinum alloy wire having a cross-sectional diameter of approximately 0.0005–0.005 inch, for example. The helical wire may have other cross-sectional shapes and be formed of different materials, such as Nitinol, for example. Coil (26) is preferably sized so that when in its free (uncompressed state) it extends the length of wire (34) with one end adjacent an enlarged portion (36 or 38) at the proximal end of the wire and the other end adjacent enlarged portion (38 or 36) at the distal end of the wire. It is to be understood that the coil may not extend the full length of the wire. For example, a flange or similar device may be provided on an intermediate portion of wire (34) to limit movement of the coil along the length of the wire.

When coil (26) is in its free state (with the wire in its undeformed configuration), loops of the coil are generally spaced from one another and do not exert any significant force on the wire (34). When the coil (26) is compressed (with the wire (34) in its deformed configuration), loops of the coil on the inner portion of the coil are squeezed together with a tight pitch so that the loops are contiguous with one another while loops on the outer portion of the coil are spaced from one another. This is due to the compressed inner arc length of coil (26) and the expanded outer arc length of the coil. The compression of the loops on the inner portion of coil (26) exerts a force on the inner side of wire (34) which forces the wire to spread open (i.e., tends to straighten the wire from its closed configuration to its open configuration).

According to a further aspect of the occlusion device as shown in FIGS. 18A–18B, a cylindrical sheath (850) is used to protect the membrane (800) from being punctured by the needles (722, 725), if the fasteners (721) are not attached to the membrane (800) and need to be inserted after the membrane is inflated. In order to be sufficiently flexible and yet to have the necessary tensile strength, the membrane (800) (see FIG. 18A, for example) is preferably made of polymeric materials such as polyethylene terephthalate, polyethylene and polyurethane. It is preferable that the membrane be compliant, yet tough enough to allow manipulation without failure. The membrane is fixed (by gluing or similar method) to the inner cylinder (727) at its proximal end and the sheath (850) is axially fixed to the membrane (800).

In order to facilitate the expansion of the sheath (850) with the membrane to occlude the opening in the vessel wall, the sheath (850) overlaps itself in a roll-up fashion, as shown in FIG. 18C. The sheath (850) is expanded and unrolled by the expansion of the membrane (800). The sheath (850) unrolls so as to cover the circumference of the expanded membrane (800) as it expands, so as to fully cover the membrane (800) in its expanded position (FIG. 18B).

Figure 18E:
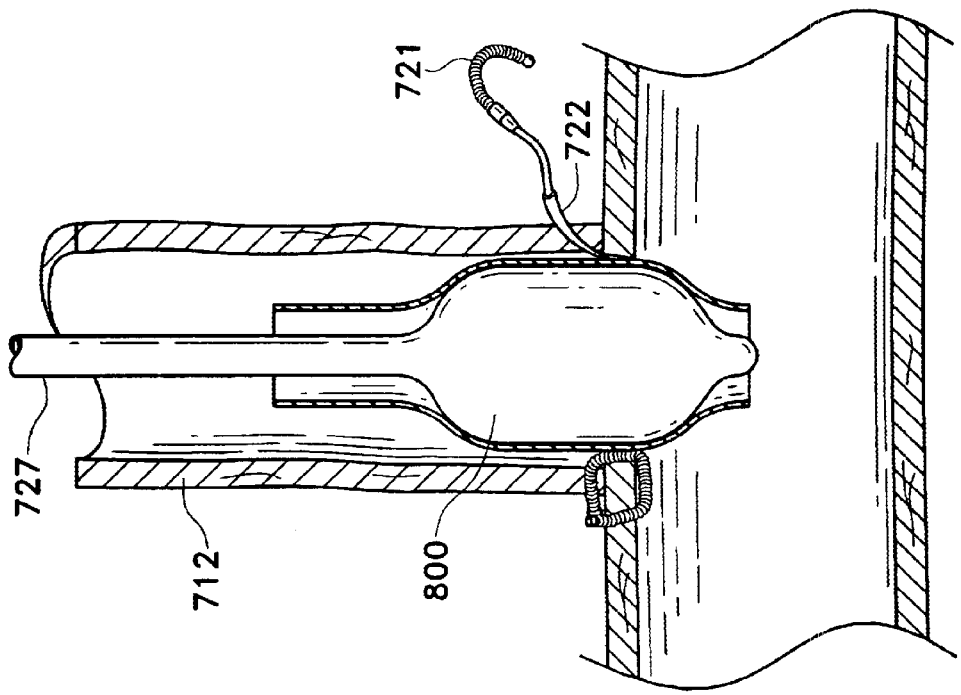
FIG. 18E is a sectional view of the device of FIG. 18A with the graft attached to the vessel by a plurality of fasteners.
Figure 18D:
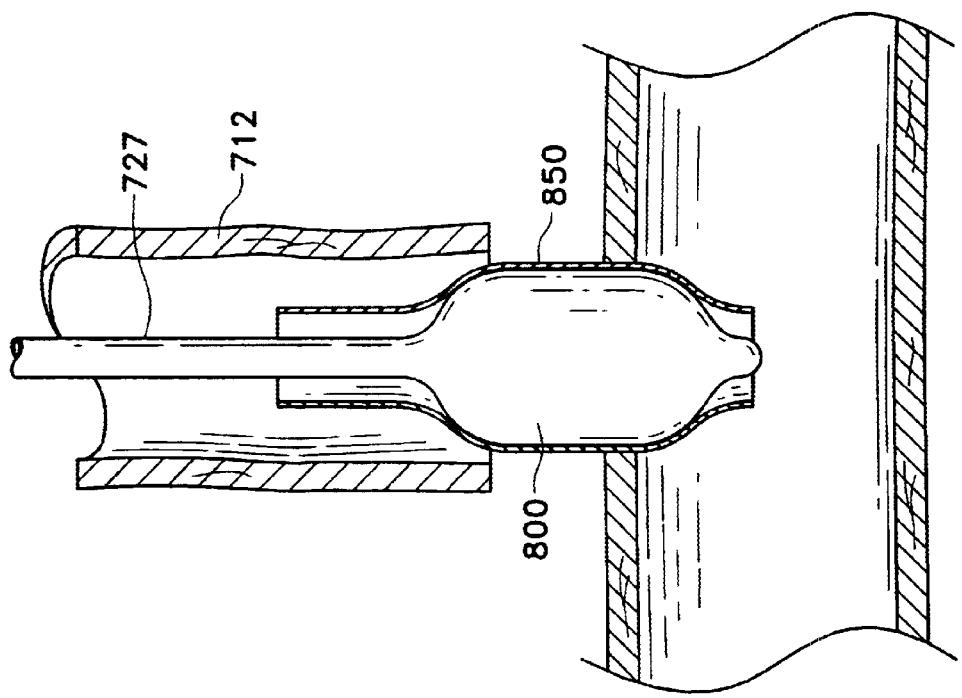
FIG. 18D is a sectional view of the device of FIG. 18A, with a graft being slid down for anastomosis.

After occlusion of the opening by the membrane (800) and the sheath (850), the punch (704) and the outer cylinder (726) can be withdrawn and a graft (712) is slid down (FIG. 18D). A plurality of fasteners (721) are inserted to attach the graft to the vessel (FIG. 18E). As the final step, the membrane (800) is then deflated and withdrawn along with the sheath (850).

The sheath (850) may be made of superelastic materials such as Nitinol or stainless steel, etc. as described above. Alternatively, the sheath may be made of polymeric materials, e.g., thin polycarbonate, polyurethane, etc. In order to facilitate the expansion of the sheath with the membrane, it is preferable that the sheath has a wall thickness of less than about 0.5 mm.

According to another further aspect of the occlusion device as illustrated in FIG. 19A, the radially expandable member comprises a plurality of expansion members (854), preferably made from a superelastic material, e.g. Nitinol, attached to the distal end of the inner cylinder (727). Solid attachment may be achieved by use of glue materials or by welding or fusion of the two. FIG. 19B illustrates the radially expandable member in a compressed state within the outer cylinder (726).

Each expansion member is attached to its adjacent members by a membrane (860). The membrane is held to the expansion member by e.g., glue, sandwich construction or other equivalent known techniques. The expansion members are arranged in a radially projecting pattern from the distal end of the inner cylinder (726) so that they can expand outwardly and form an umbrella when they exit the outer cylinder (726) (FIG. 18B). This creates an occlusion of the vessel wall opening. The expansion members are curved to present a convex surface so as to better withstand the pressure inserted by the blood flow.

The membrane (860) can be made in any suitable material which can block flow of fluid, particularly blood, therethrough. In choosing the material for the membrane, factors such as strength, flexibility, or bonding to the expansion elements should be considered. For example, the membrane may comprise latex, silicone, PET, etc.

Figure 20E:
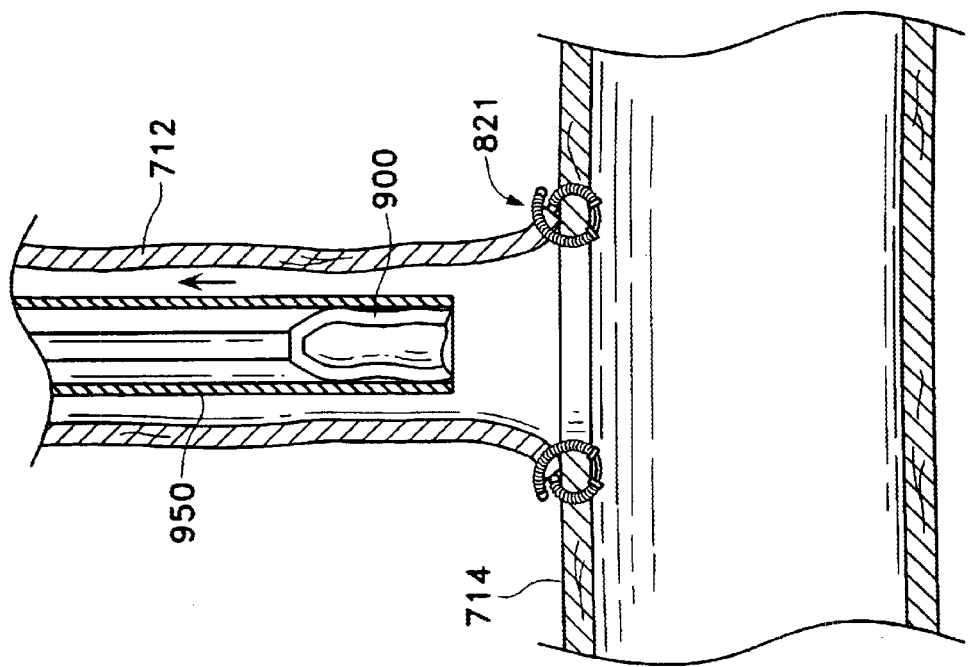
FIG. 20E is a sectional view of the device of FIG. 20A with the punch or cutting member retrieved and a graft in place and partially anastomosed to the vessel.

In another example of the present invention shown in FIGS. 20A–20F, an occlusion device is provided with an adapter (794) that temporarily holds a plurality of needles (725') to be driven through the wall of the vessel (714). The procedure for preparing the opening in the wall of the vessel (714) is essentially the same as that described above with regard to FIGS. 15A and 15B, for example, with the exception that the tube of the cutting member or punch (704') is much shorter than the tube of the cutting member or punch (704), and is adapted to receive an adapter, preferably a tubular adapter (740) as shown in FIG. 20A. The cutting member (704') is preferably made of a biocompatible metal such as stainless steel, Nitinol, titanium alloys, or the like, much the same as the cutting member (704), and similarly has a distal cutting edge.

The adapter (740), on the other hand, is preferably made of biocompatible plastics, such as ABS, polyurethanes, polycarbonates, or other medically compatible and acceptable polymers, for ease and less expense in manufacturing, although the adapter (740) may also be formed of the same metals used in making the cutting member (704'). The adapter (740) has about the same outside diameter as the tube of the cutting member (704'), or if slightly larger in diameter, is tapered (742) so as to facilitate the insertability of the adapter through the opening in the vessel (714). The walls of the adapter (740) are provided with bores or wells (744) that are dimensioned to snugly hold needles (725') therein. The wells (744) may be mechanically formed in the adapter (740) as by boring, melting, electrodischarge machining, etc., or may be molded in during the formation of the adapter, for example. The wells (744) are formed so as to fit closely enough with the needles (725') so as to maintain the needles at the desired angular orientation with respect to the longitudinal axis of the adapter (740), but not so tight as to form an impediment to their removal by hand or with a hand tool at the appropriate time during the procedure. The adapter orients the needles at an angle of between about 10 and 45 degrees. In one preferred example, the angle is about 30 degrees.

After formation of the opening in the vessel (714) wall and removal of the tissue plug (734) using anchor member (728) and disk (720), as shown in FIG. 20A and described above, the adapter (740) is driven to insert the cutting member (704') further and entirely within the vessel (714) and to insert a portion of the adapter (740) into the vessel (714), to the extent that the needles (725') are within the vessel (714) and positioned to pierce the inner wall of the vessel (714), as shown in FIG. 20B. The needles (725') flex inwardly and approach the wall of the adapter as they pass through the opening in the vessel, and then resume their previous orientation once they have completed cleared the wall of the vessel (714) as shown in FIG. 20B. The adapter (740) preferably holds four to eight needles (725') which are equidistantly spaced circumferentially around the adapter, although certainly more than eight, and likely less than four needles could be successfully used, as would be apparent to one of ordinary skill in the art, after reading the present disclosure.

In this embodiment, the needles (725') preferably, although not necessarily, differ from needles (721) in that the needles (725') are preferably substantially straight, while needles (721) are preferably curved. Further, this embodiment preferably, although not necessarily, uses two-stage release fasteners (821) for sequentially fastening the anastomosis as further described below.

Figure 21A:
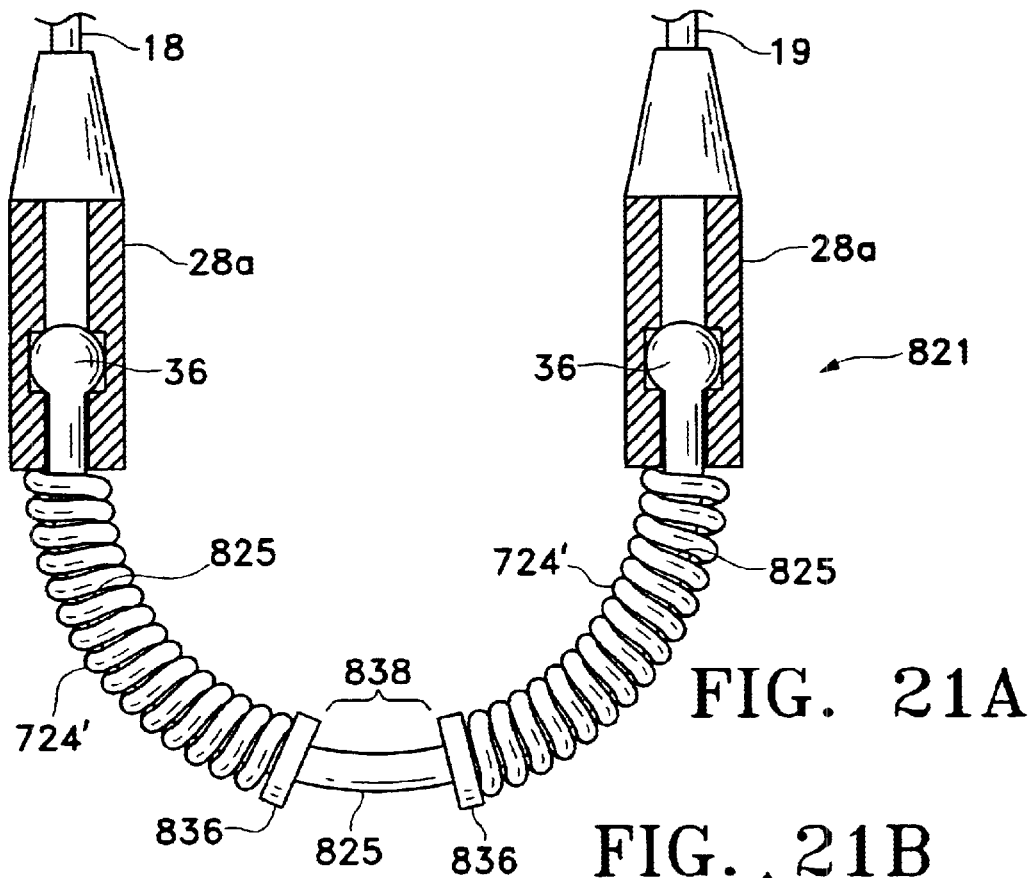
FIG. 21A is a partial schematic drawing of a two-stage release fastener for use with the proximal anastomosis device of FIGS. 20A–20F, for example.

Turning to FIG. 21A, a partial schematic view of a two-stage release fastener (821) is shown. The fastener (821) includes a deformable wire (825) made of a shape memory alloy, such as that described above with regard to fasteners (721). The deformable wire preferably includes enlarged portions (36) at opposite ends and which are substantially identical to one another. Retainers (836) are swedged or welded onto the wire (825) after compression of coils (724') as described further below.

Coils (724') are substantially the same as any of the coils (724) or (26) described above with the exception of being shorter to allow serial placement of two coils (724') on a single wire (825) to enable separate and independent actuation and closing of opposite sides of the fastener (721). Release mechanisms (28a), which are preferably, but not necessarily the same, are releasably coupled to the respective enlarged ends (36) at opposite ends of the wire (825), and are, in turn coupled to the needles (722) and (725) by flexible members (18) and (19) respectively. The release mechanisms (28a) in this embodiment are preferably cable type release mechanisms, as described in copending application Ser. No. 09/259,705 entitled "Tissue Connector Apparatus with Cable Release", and as shown above in FIG. 17F, for example, although other release mechanisms such as described herein and in those documents incorporated by reference can also be used.

Assembly of the fastener (821) into the open position as shown in FIG. 21A is performed by first forming the wire (825) to set its shape memory and to form an enlarged portion (36) at one end thereof, preferably by an electric discharge technique. Other methods of forming the enlarged portion, as well as methods of setting the memory shape of the wire (825) are described in detail in commonly assigned application entitled "Multiple Bias Surgical Fastener" which is being filed concurrently herewith and therefor does not yet have an application serial number, and in copending and commonly assigned application Ser. No. 09/090,305.

A first coil (724') is next slid over the wire (825) and an end of the coil (724') is abutted against or placed adjacent to the enlarged portion (36). Next, a first retainer (836) is slid over the wire (825) and abutted against the opposite end of the coil (724'), after which a second retainer (836) is slid over the wire and placed adjacent the first retainer (836). A second coil (724') is then slid over the wire (825) and a first end is abutted against the second retainer (836), while the second end of the second coil (724') is used to determine where the wire (825) is cut to length. Generally, the wire (825) is cut so that it extends far enough, so that once the enlarged portion is formed at the end, the first and second portions are symmetric.

After cutting to length, the second end of the wire (825) is formed into an enlarged portion (836), preferably by electrodischarge. A first release mechanism (28a) is next fitted over the first enlarged portion (36), preferably according to the techniques described in copending application Ser. No. 09/259,705 with regard to the cable release. The first retainer (836) is then slid against the coil (724') to compress it to a position that forces the first side of the fastener into its open configuration. The first retainer (836) is then swedged at its location to maintain the first portion of the fastener in the open position. Although swedging is preferred, welding or other equivalent methods of fixation may also be used to fix the retainer in place.

Likewise, a second release mechanism (28a) is fitted over the second enlarged portion (36), and the second retainer (836) is then slid against the second coil (724') to compress it to a position that forces the second side of the fastener into its open configuration. The second retainer (836) is then swedged at its location to maintain the second portion of the fastener in the open position, which results in the entire fastener (821) now being in its open position, as shown in FIG. 21A. The placement and fixation of the retainers (836) results in the formation of a gap (838) therebetween.

Figure 21B:
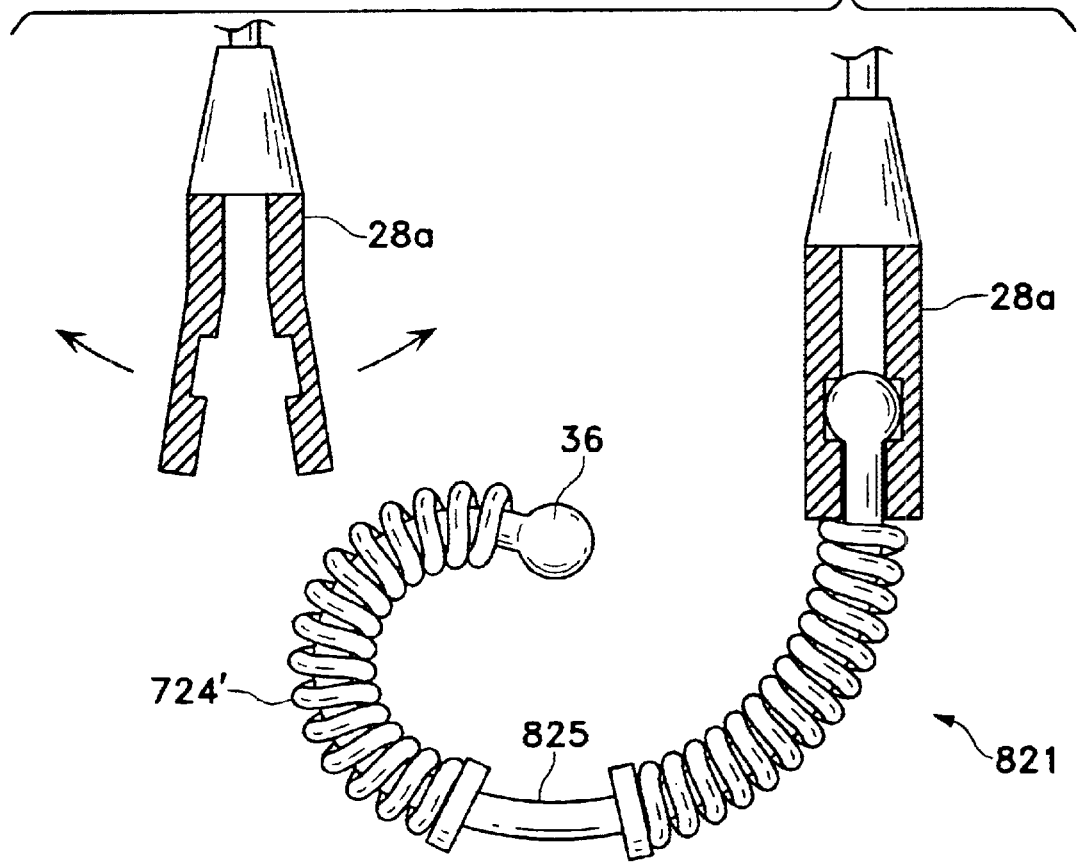
FIG. 21B is a partial schematic view of the fastener of FIG. 21A after one end of the fastener has been released.

Actuation of the first release mechanism (28a) is by squeezing or compression of a portion of the mechanism, which causes it to open, thereby releasing the enlarged portion (36). This, in turn allows a re-expansion of the coil (724') thereby relieving the opening stresses against the first portion of the wire (825), thereby allowing the memory set of the wire (825) (and the memory set of the coil (724') when a double memory configuration is used) to return the first portion of the wire (825) to the closed or memory position, as shown in FIG. 21B.

Figure 21C:
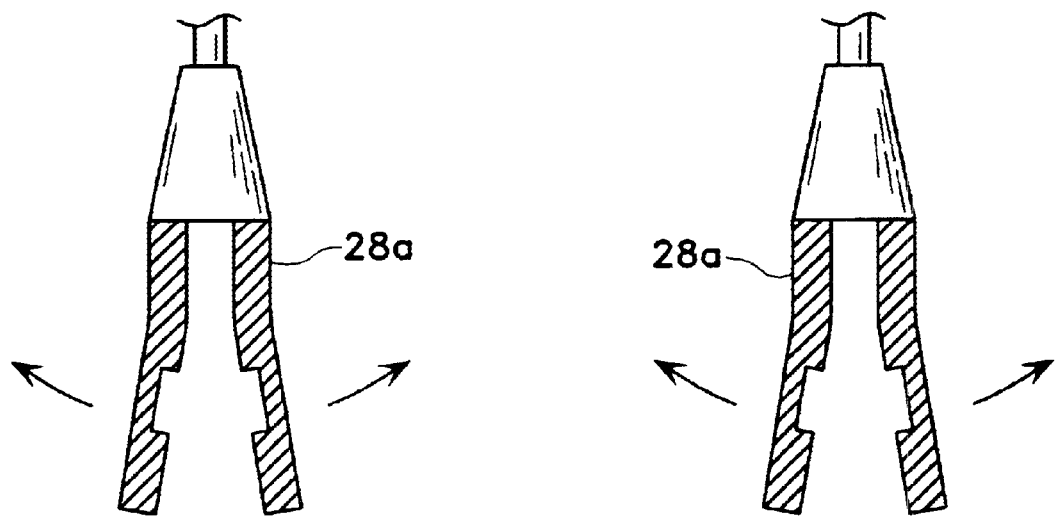
FIG. 21C is a partial schematic view of the fastener of FIG. 21A after both ends of the fastener have been released.
Figure 21C:
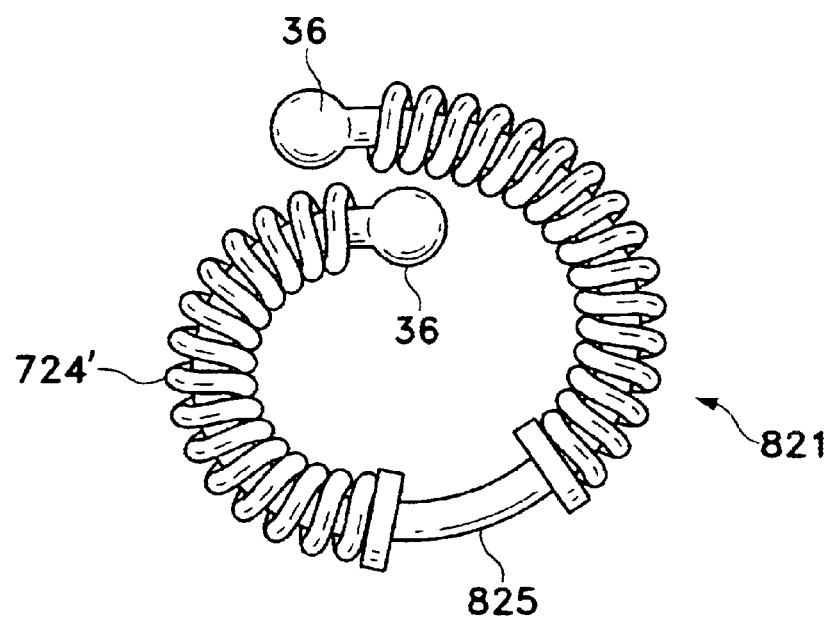
Figure 21C:

Actuation of the second release mechanism (28a) is performed independently of the first release mechanism, and therefor allows an independent closing of the second portion of the fastener (821), as shown in FIG. 21C. The mechanism for closing the second portion is preferably the same as that described above for closing of the first portion.

Returning to FIG. 20B, the adapter, and thus the entire assembly, is next pulled back some so as to pierce the wall of the vessel (714) with each of the needles (725'). Once the needles have fully penetrated the vessel wall and protrude through the outside wall of the vessel, the adapter is maintained in its position, and the needles (725') are pulled all the way through the wall of the vessel (714), one at a time, to position the fasteners (821), an example of which is shown in FIG. 20C. A flexible sealing member, such as radially expandable member (730), for example, or cylindrical sheath (850) and membrane (800), or a cylindrical restraining sheath (900) and expandable, flexible sealing member (950) (FIG. 20C), or other occluding member as described herein, is then inserted. The restraining sheath (950) may be formed of the same materials as described above with regard to sheath (850) and the flexible sealing member may be formed from the same materials as described above with regard to radially expandable member (730) or membrane (860). The straight needles (725') and flexible members (19) are then removed from the fasteners (821) by releasing the release mechanisms (28a) attached thereto, from the respective enlarged portions (36) as described above. This closes the first portion of each fastener (821) thereby fixing them in position in the location of the vessel wall, as exemplified in FIG. 20D.

Once the fasteners (821) have been fixed into the wall of the vessel (714), the flexible sealing member (900) is expanded to establish the occlusion by removing the restraining sheath (950) from its restraining position, as shown in FIG. 20D. The tube cutter assembly, including the cutting member or punch (704') and the adapter (740) are then withdrawn from the vessel, as shown in FIG. 20D, and removed from overlying the restraining sheath (950).

After removal of the tube cutter assembly, a graft (712) is positioned over the restraining sheath (950) and into position at the anastomosis site as shown in FIG. 20E. The needles (722) are next used to pierce the walls of the graft (712) from inside to outside, and then pulled through entirely to position the second portions of the fasteners (821) in the wall of the graft (712). Once the fasteners are positioned, the needles (722) and flexible members (18) are removed from the respective fasteners (821) to close the second portions of the fasteners (821) in the same manner as described above with regard to closing of the first portions of the fasteners (821).

Figure 20F:
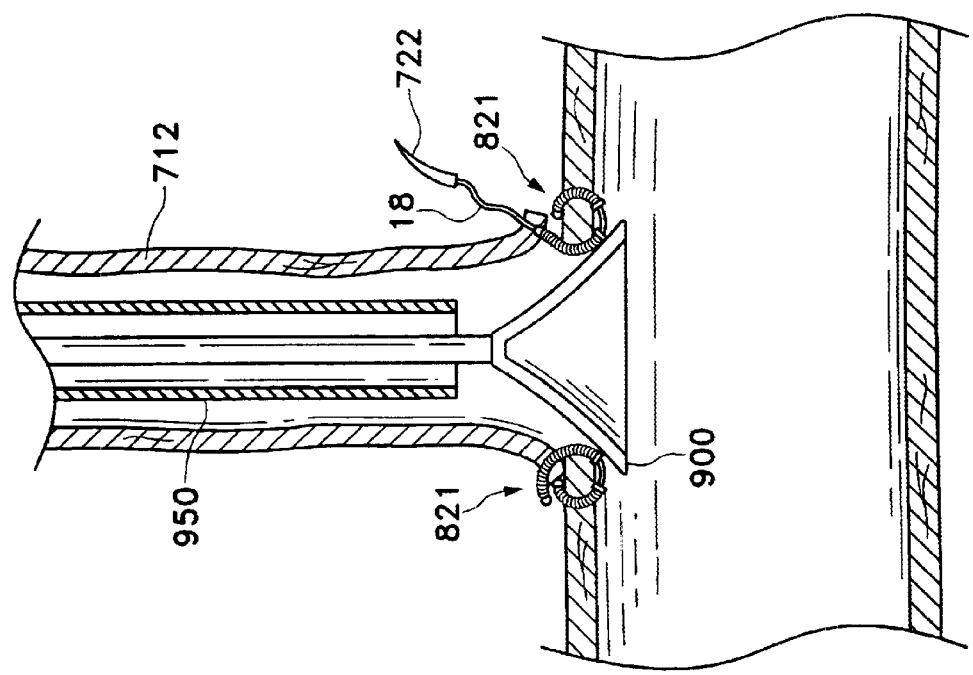
FIG. 20F is a sectional view of the device of FIG. 20A with the graft having been anastomosed to the vessel and with the occluding device being withdrawn.

After all of the fasteners (821) have been fully closed to complete the approximation and anastomosis of the vessel (714) and graft (712), the restraining sheath (950) is slid back down over the flexible sealing member (900) to compress it and surround it as shown in FIG. 20F. The restraining sheath (950), together with the flexible sealing member (900) therein, are then pulled away together so as to be removed from the anastomosis site and the graft. This completes the anastomosis procedure.

The above is a detailed description of particular embodiments of the invention. It is recognized that departures from the disclosed embodiments may be made within the scope of the invention and that obvious modifications will occur to a person skilled in the art. The full scope of the invention is set out in the claims that follow and their equivalents. Accordingly, the claims and specification should not be construed to unduly narrow the full scope of protection to which the invention is entitled.

What is claimed is:

1. An anastomosis system comprising: a tubular member having an end with an edge adapted to form an opening in a vessel wall; and an occlusion member adapted to be slidably coupled to the tubular member and adapted to substantially occlude said opening in the vessel wall to form an area of hemostasis, further comprising an anchor member adapted to hold said vessel wall in place while the tubular member is forming said opening in, said vessel wall, said anchor member being slidably coupled to the tubular member, wherein the anchor member comprises a shaft and a piercing member extending from a distal end of said shaft, said piercing member being adapted to pierce the vessel wall, further comprising a generally circular centering disk slidably movable along said shaft.

2. The anastomosis system of claim 1 wherein said shaft comprises flexible polymeric material.

3. The anastomosis system of claim 1 wherein the shaft has a diameter of less than 3 mm.

4. The anastomosis system of claim 1 wherein the piercing member has a tapered end.

5. The anastomosis system of claim 1 wherein the piercing member has a pointed end.

6. The anastomosis system of claim 1 wherein said centering disk comprises ABS or polyurethane.

7. The anastomosis system of claim 1 wherein the centering disk comprises one or more spikes extending from a surface of the centering disk proximal of the vessel wall.

8. The anastomosis system of claim 7 wherein said one or more spikes comprise Nitinol.

9. The anastomosis system of claim 7 wherein said one or more spikes have lengths of less than about 5 mm.

10. The anastomosis system of claim 1 wherein the centering disk is made from a medically acceptable polymer.

11. Anastomosis apparatus comprising a tubular member having an end with an edge adapted to form an opening in a vessel wall, further comprising an anchor member adapted to hold said vessel wall in place while the tubular member is forming said opening in said vessel wall, said anchor member being slidably coupled to the tubular member, wherein the anchor member comprises a shaft and a piercing member extending from a distal end of said shaft, said piercing member being adapted to pierce the vessel wall, further comprising a generally circular centering disk slidably movable along said shaft.

12. The anastomosis apparatus of claim 11 wherein said shaft comprises a flexible polymeric material.

13. The anastomosis apparatus of claim 11 wherein the shaft has a diameter of less than 3 mm.

14. The anastomosis apparatus of claim 11 wherein the piercing member has a tapered end.

15. The anastomosis apparatus of claim 11 wherein the piercing member has a pointed end.

16. The anastomosis apparatus of claim 11 wherein said centering disk comprises ABS.

17. The anastomosis apparatus of claim 11 wherein said centering disk comprises polyurethane.

18. The anastomosis apparatus of claim 11 wherein said centering disk has one or more spikes extending from a surface thereof and adapted to engage said vessel wall.

19. The anastomosis apparatus of claim 18 wherein said one or more spikes comprise Nitinol.

20. The anastomosis apparatus of claim 18 wherein said one or more spikes have a length of less than about 5 mm.

21. Anastomosis apparatus comprising a tubular member having an end with an edge adapted to form an opening in a vessel wall, further comprising an elongated member slidably disposed in said tubular member, said elongated member comprising a shaft and a piercing member adapted to pierce said vessel wall, said shaft having a proximal end and a distal end, and said piercing member extending from the distal end of said shaft, further including a disk slidably coupled to said elongated member, further including one or more spikes extending from said disk.

22. The anastomosis apparatus of claim 21 wherein said piercing member has a tapered end.

23. The anastomosis apparatus of claim 21 wherein said piercing member has a pointed end.

24. The anastomosis apparatus of claim 21 wherein said shaft comprises a flexible polymeric material.

25. The anastomosis apparatus of claim 21 wherein the shaft has a diameter of less than 3 mm.

26. Anastomosis apparatus comprising a tubular member, an anchor member slidably mounted in said tubular member, and a sliding member slidably coupled to said anchor member, said tubular member having an end with a cutting edge adapted to form an opening in a vessel wall, said anchor member comprising a shaft and a piercing member extending therefrom, said piercing member having a pointed tip and a least one barb, and said sliding member being movable toward said piercing member to hold severed vascular tissue therebetween.

27. The anastomosis apparatus of claim 26 further including means for preventing backsliding of said sliding member away from said piercing member.

28. The anastomosis apparatus of claim 26 wherein said sliding member includes members extending therefrom for gripping the tissue of the vessel.

29. The anastomosis apparatus of claim 26 wherein said sliding member centers said shaft in said tubular member.

30. The anastomosis apparatus of claim 26 wherein said sliding member comprises a disk.

* * * * *

UNITED STATES PATENT AND TRADEMARK OFFICE
CERTIFICATE OF CORRECTION

PATENT NO. : 6,695,859 B1
APPLICATION NO. : 09/540636
DATED : February 24, 2004
INVENTOR(S) : Golden et al.

It is certified that error appears in the above-identified patent and that said Letters Patent is hereby corrected as shown below:

The Title page item (75) Inventors should read as follows:

Steve Golden, Menlo Park, CA (US);

Liem Ho, Mountain View, CA (US)

Signed and Sealed this

Eighth Day of August, 2006

JON W. DUDAS
*Director of the United States Patent and Trademark Office*